US012648768B2

(12) United States Patent
Bowman et al.

(10) Patent No.:  US 12,648,768 B2
(45) Date of Patent:       Jun. 9, 2026

---

(54) LARGE PUSH-IN SUTURE ANCHOR

(71) Applicant: Responsive Arthroscopy, Inc., Minneapolis, MN (US)

(72) Inventors: Brian Bowman, Carlsbad, CA (US); Jonathon Gold, Solana Beach, CA (US); Jacob Hustedt, Sandy, UT (US); Benjamin Arnold, San Diego, CA (US); Douglas Kohrs, Minneapolis, MN (US); Kimberly Bahoora, Medina, MN (US)

(73) Assignee: Responsive Arthroscopy, Inc., Minneapolis, MN (US)

( * ) Notice: Subject to any disclaimer, the term of this patent is extended or adjusted under 35 U.S.C. 154(b) by 615 days.

(21) Appl. No.: 17/401,263

(22) Filed: Aug. 12, 2021

(65) Prior Publication Data

US 2022/0054122 A1      Feb. 24, 2022

Related U.S. Application Data

(63) Continuation of application No. PCT/US2021/045506, filed on Aug. 11, 2021.
(Continued)

(51) Int. Cl.
*A61B 17/04*          (2006.01)
*A61F 2/08*           (2006.01)

(52) U.S. Cl.
CPC ........ *A61B 17/0401* (2013.01); *A61F 2/0811* (2013.01); *A61B 2017/0409* (2013.01);
(Continued)

(58) Field of Classification Search
CPC ........ A61B 17/0401; A61B 2017/0409; A61B 2017/0414; A61B 2017/044;
(Continued)

(56) References Cited

U.S. PATENT DOCUMENTS

| | | | |
|---|---|---|---|
| 545,760 | A | 9/1895 | Ashley |
| 3,845,575 | A | 11/1974 | Boden |

(Continued)

FOREIGN PATENT DOCUMENTS

| | | |
|---|---|---|
| EP | 3138505 A1 | 3/2017 |
| EP | 3235471 A1 | 10/2017 |

(Continued)

OTHER PUBLICATIONS

U.S. Appl. No. 16/569,752, filed Sep. 13, 2019, U.S. Pat. No. 11,298,120, Apr. 12, 2022.
(Continued)

*Primary Examiner* — Kathleen S Holwerda
*Assistant Examiner* — James R Mcginnity
(74) *Attorney, Agent, or Firm* — Goodwin Procter LLP

(57)          ABSTRACT

A suture anchor system comprising an anchor and an insert, and methods of use are provided. The anchor body has proximal and distal ends, and opposite first and second lateral sides extending between the proximal end and the distal end. A suture passage comprising a proximal surface and a distal surface extends through the anchor body from a first opening in the first lateral side to a second opening in the second lateral side. A channel extends along a longitudinal axis of the anchor body from a proximal opening in the proximal end of the anchor body to a distal opening in the proximal surface of the suture passage. The channel does not extend past the distal surface of the suture passage. The insert is configured to translate longitudinally within the channel between the proximal end of the anchor body and the distal surface of the suture passage.

17 Claims, 35 Drawing Sheets

Related U.S. Application Data

(60) Provisional application No. 63/067,779, filed on Aug. 19, 2020.

(52) U.S. Cl.
CPC . *A61B 2017/0414* (2013.01); *A61B 2017/044* (2013.01); *A61B 2017/0445* (2013.01); *A61B 2017/0448* (2013.01); *A61B 2017/0464* (2013.01); *A61F 2002/0841* (2013.01)

(58) Field of Classification Search
CPC .... A61B 2017/0445; A61B 2017/0448; A61B 2017/0464; A61B 2017/042; A61B 2017/0421; A61B 2017/0422; A61B 2017/0423; A61B 2017/0424; A61B 2017/0425; A61B 2017/0426; A61B 2017/0427; A61B 2017/0429; A61B 2017/043; A61B 2017/0431; A61B 2017/0432; A61B 2017/0433; A61B 2017/0446; A61B 2017/0451; A61F 2/0811; A61F 2002/0841; A61F 2002/0823; A61F 2002/0829
See application file for complete search history.

(56) References Cited

U.S. PATENT DOCUMENTS

| | | | |
|---|---|---|---|
| 3,953,144 A | 4/1976 | Boden | |
| 6,185,798 B1 | 2/2001 | Ton | |
| 6,585,730 B1 | 7/2003 | Foerster | |
| 7,637,926 B2 | 12/2009 | Foerster et al. | |
| 7,713,286 B2 | 5/2010 | Singhatat | |
| 8,100,923 B2 | 1/2012 | Paraschac et al. | |
| 8,133,258 B2 | 3/2012 | Foerster et al. | |
| 8,162,978 B2 | 4/2012 | Lombardo et al. | |
| 8,371,004 B2 | 2/2013 | Huber et al. | |
| 8,409,252 B2 | 4/2013 | Lombardo et al. | |
| 8,652,173 B2 | 2/2014 | Mansmann | |
| 8,790,346 B2 | 7/2014 | Daniels et al. | |
| 9,168,034 B2 | 10/2015 | Lombardo et al. | |
| 9,226,742 B2 | 1/2016 | Wolf et al. | |
| 9,241,706 B2 | 1/2016 | Paraschac et al. | |
| 9,277,910 B2 | 3/2016 | Nason et al. | |
| 9,295,460 B2 | 3/2016 | Hoof et al. | |
| 9,345,467 B2 | 5/2016 | Lunn et al. | |
| 9,402,617 B2 | 8/2016 | Baird | |
| 9,463,010 B2 | 10/2016 | Gittings et al. | |
| 9,687,224 B2 | 6/2017 | Lunn et al. | |
| 9,936,939 B2 | 4/2018 | Nguyen et al. | |
| 10,076,377 B2 | 9/2018 | Bonutti et al. | |
| 10,159,477 B2 | 12/2018 | Lunn et al. | |
| 10,238,377 B2 | 3/2019 | Nason et al. | |
| 11,298,120 B2 | 4/2022 | Bowman et al. | |
| 11,510,665 B2 | 11/2022 | Hustedt | |
| 12,178,425 B2 | 12/2024 | Hustedt | |
| 2003/0195563 A1 | 10/2003 | Foerster | |
| 2005/0119663 A1 | 6/2005 | Keyer et al. | |
| 2006/0265010 A1 | 11/2006 | Paraschac et al. | |
| 2006/0282119 A1 | 12/2006 | Perchik | |
| 2007/0060922 A1 | 3/2007 | Dreyfuss | |
| 2007/0162033 A1 | 7/2007 | Daniels et al. | |
| 2007/0213770 A1 | 9/2007 | Dreyfuss | |
| 2007/0276437 A1 | 11/2007 | Call et al. | |
| 2008/0051836 A1 | 2/2008 | Foerster et al. | |
| 2008/0275469 A1* | 11/2008 | Fanton | A61B 17/0487 606/232 |
| 2008/0294204 A1 | 11/2008 | Chirico et al. | |
| 2009/0012522 A1 | 1/2009 | Lob | |
| 2009/0012571 A1 | 1/2009 | Perrow et al. | |

| | | | |
|---|---|---|---|
| 2009/0082807 A1 | 3/2009 | Miller et al. | |
| 2009/0292321 A1 | 11/2009 | Collette | |
| 2009/0312794 A1 | 12/2009 | Nason et al. | |
| 2010/0004683 A1 | 1/2010 | Hoof et al. | |
| 2011/0004242 A1 | 1/2011 | Stchur | |
| 2011/0009885 A1 | 1/2011 | Graf et al. | |
| 2011/0112576 A1 | 5/2011 | Nguyen et al. | |
| 2011/0166599 A1 | 7/2011 | Jervis et al. | |
| 2011/0238113 A1 | 9/2011 | Fanton et al. | |
| 2012/0101526 A1* | 4/2012 | Bennett | A61B 17/842 606/232 |
| 2012/0123474 A1 | 5/2012 | Zajac et al. | |
| 2013/0030479 A1 | 1/2013 | Regauer | |
| 2013/0123841 A1 | 5/2013 | Lyon | |
| 2013/0144334 A1 | 6/2013 | Bouduban et al. | |
| 2013/0197578 A1 | 8/2013 | Gregoire et al. | |
| 2014/0081323 A1 | 3/2014 | Hawkins | |
| 2014/0257294 A1 | 9/2014 | Gedet et al. | |
| 2014/0379028 A1* | 12/2014 | Lo | A61B 17/0401 606/232 |
| 2016/0030035 A1 | 2/2016 | Zajac et al. | |
| 2016/0089131 A1 | 3/2016 | Wade | |
| 2016/0100833 A1 | 4/2016 | Lunn et al. | |
| 2016/0157852 A1 | 6/2016 | Dougherty et al. | |
| 2016/0235398 A1 | 8/2016 | Nguyen et al. | |
| 2016/0302785 A1 | 10/2016 | Nason et al. | |
| 2017/0065273 A1 | 3/2017 | Hart et al. | |
| 2017/0189007 A1 | 7/2017 | Burkhart et al. | |
| 2017/0303910 A1 | 10/2017 | Niver | |
| 2018/0008256 A1 | 1/2018 | Fallin et al. | |
| 2018/0146959 A1 | 5/2018 | Gerber et al. | |
| 2018/0249998 A1 | 9/2018 | Chavan et al. | |
| 2018/0368827 A1* | 12/2018 | Balboa | A61B 17/0401 |
| 2019/0038275 A1* | 2/2019 | Clark | A61F 2/0811 |
| 2019/0117377 A1 | 4/2019 | Ticker | |
| 2019/0167254 A1* | 6/2019 | Balboa | A61B 17/0401 |
| 2019/0175223 A1 | 6/2019 | Nguyen et al. | |
| 2019/0343507 A1 | 11/2019 | Chavan et al. | |
| 2019/0380695 A1 | 12/2019 | Fallin et al. | |
| 2019/0380747 A1 | 12/2019 | Fischer et al. | |
| 2020/0077999 A1 | 3/2020 | Bowman et al. | |
| 2020/0245997 A1* | 8/2020 | Balboa | A61B 17/0401 |
| 2022/0167963 A1 | 6/2022 | Hustedt | |
| 2022/0192655 A1 | 6/2022 | Bowman et al. | |
| 2023/0210516 A1 | 7/2023 | Hustedt | |
| 2023/0320720 A1 | 10/2023 | Bahoora et al. | |
| 2023/0320721 A1 | 10/2023 | Bahoora et al. | |

FOREIGN PATENT DOCUMENTS

| | | | |
|---|---|---|---|
| WO | WO-2020056029 A1 | 3/2020 | |
| WO | WO-2021202123 A1 | 10/2021 | |
| WO | WO-2022039991 A1 | 2/2022 | |
| WO | WO-2023044295 A1 | 3/2023 | |

OTHER PUBLICATIONS

U.S. Appl. No. 17/654,170, filed Mar. 9, 2022.
U.S. Appl. No. 17/651,747, filed Feb. 18, 2022, U.S. Pat. No. 11,510,665, Nov. 29, 2022.
U.S. Appl. No. 18/046,439, filed Oct. 13, 2022.
U.S. Appl. No. 18/335,911, filed Jun. 15, 2023.
U.S. Appl. No. 18/335,914, filed Jun. 15, 2023.
PCT/US2019/050659 International Search Report dated Dec. 31, 2019.
PCT/US2021/023101 International Search Report and Written Opinion mailed Jun. 24, 2021.
PCT/US2021/045506 International Search Report and Written Opinion dated Jan. 31, 2022.
PCT/US2022/076334 International Search Report and Written Opinion mailed Dec. 13, 2022.

* cited by examiner

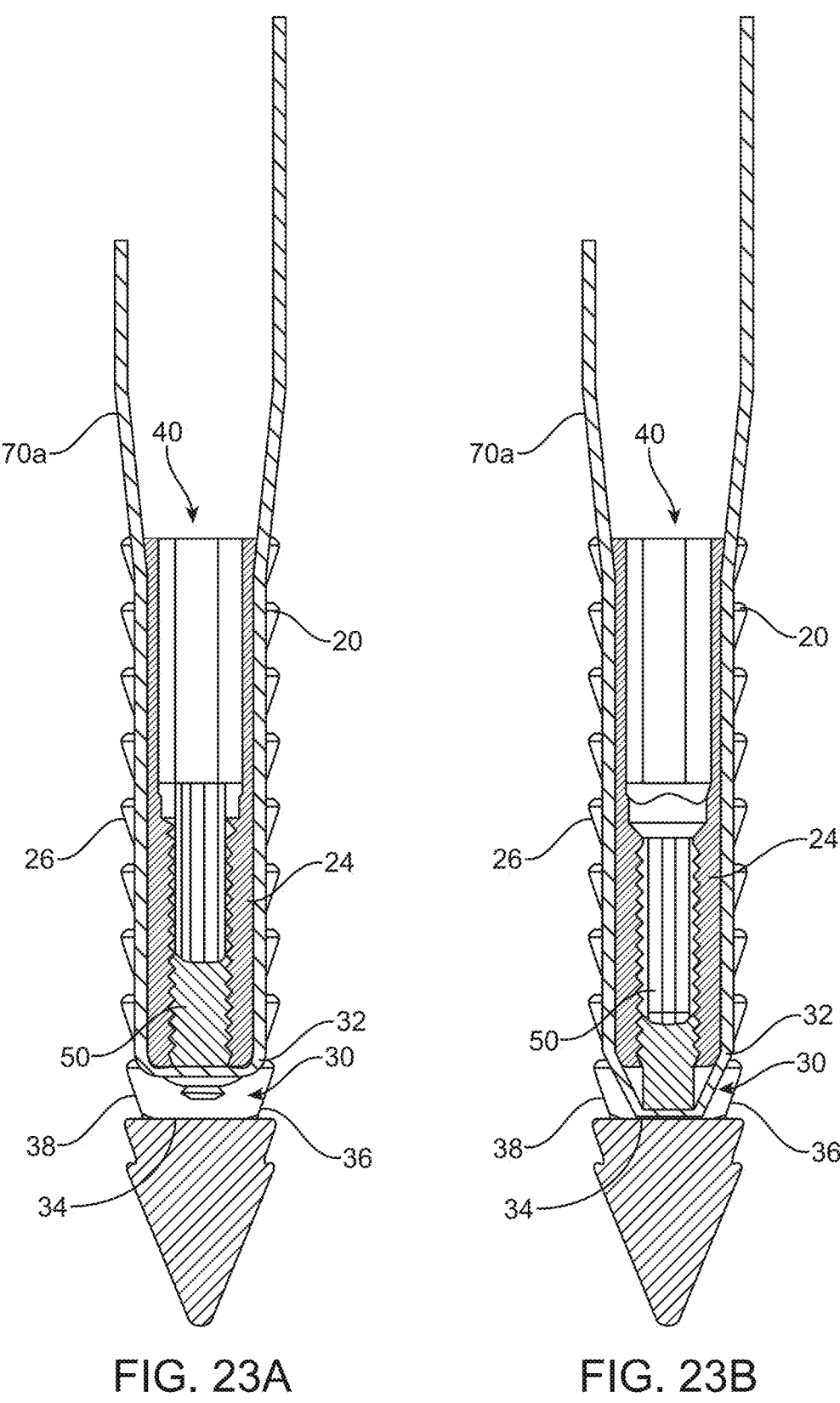
FIG. 23A                    FIG. 23B

LARGE PUSH-IN SUTURE ANCHOR

CROSS-REFERENCE

This application is a continuation application of International Application No. PCT/US21/45506, filed on Aug. 11, 2021, which claims the benefit of U.S. Provisional Application No. 63/067,779, filed on Aug. 19, 2020, which is incorporated herein by reference in its entirety.

BACKGROUND

The complete or partial detachment of ligaments, tendons, and/or other soft tissues from their associated bones within the body are relatively commonplace injuries, particularly among athletes. Tissue detachment may occur as the result of an accident such as a fall, over-exertion during a work-related activity, during the course of an athletic event, or in any one of many other situations and/or activities.

In the case of a partial detachment, the injury will frequently heal itself, if given sufficient time and if care is taken not to expose the injury to further undue stress. In the case of complete detachment, however, surgery may be needed to re-attach the soft tissue to its associated bone or bones. Suture anchors provide one type of device that may be used in helping to re-attach soft tissue to its associated bone or bones.

SUMMARY

The present disclosure generally relates to medical devices and methods and more particularly relates to suture anchors and methods for using suture anchors in attaching soft tissue to its associated bone or bones.

During surgeries where soft tissue is attached to its associated bone or bones, it is generally beneficial to be able to secure anchored suture material using tension, such as by tying a knot. However, in many situations, it is difficult for a surgeon to form a knot and thus it is beneficial to provide knotless suture anchors. While knotless suture anchors allow for surgeons to more easily secure suture materials, knotless suture anchors that are currently available often fail to provide a method for a surgeon to apply tension to the suture in the way that one may apply tension by forming a knot. As such, it would be beneficial to provide a knotless suture anchor that allows a surgeon to apply an amount of tension in the securing of the suture material to the bone. Accordingly, suture anchors, systems, and methods of using the same are provided to address this need.

Additionally, many embodiments of suture anchors that are discussed herein have been designed to preserve integrity of the suture when in use. In particular, in some embodiments, locking inserts that are used to engage a suture or sutures are configured to spread pressure across a large area while still maintaining sufficient compression of the suture to lock it in place. By spreading pressure across a large area, an insert provides less focused pressure to the suture when compared to an insert that pinches a suture at severe angles against one or more edges of a suture anchor.

Provided herein are suture anchor systems. An exemplary system comprises an anchor and an insert. The anchor comprises an anchor body having a proximal end, a distal end, a longitudinal axis, a first lateral side extending between the proximal end and the distal end, and a second lateral side extending between the proximal end and the distal end and opposite laterally of the first lateral side; a suture passage comprising a proximal surface and a distal surface and extending through the anchor body from a first opening in the first lateral side to a second opening in the second lateral side; and a channel extending along the longitudinal axis of the anchor body from a proximal opening in the proximal end of the anchor body to a distal opening in the proximal surface of the suture passage. The channel does not extend past the distal surface of the suture passage. The insert comprises an insert body having a proximal end and a distal end, wherein the insert is configured to translate longitudinally within the channel between the proximal end of the anchor body and the distal surface of the suture passage. In many embodiments, the distal surface of the suture passage is v-shaped and has a first lateral plane extending from the first opening towards a central normal plane and a second lateral plane extending from the second opening towards the central normal plane, the central normal plane being substantially perpendicular to the longitudinal axis of the anchor body. In many embodiments, the distal surface of the suture passage is substantially flat and substantially perpendicular to the longitudinal axis of the anchor body. In many embodiments, the distal surface of the suture passage is substantially flat and substantially perpendicular to the longitudinal axis of the anchor body. In many embodiments, at least a portion of the distal surface of the suture passage comprises a convex curvature extending proximally towards the distal opening of the channel. In many embodiments, a proximal portion of the convex curvature extends into the distal opening of the channel. In many embodiments, the convex curvature spans the entire distal surface. In many embodiments, the convex curvature has an arc angle within a range of about 3.5° to about 15°. In many embodiments, the distal end of the insert is shaped to correspond to the distal surface of the suture passage. In many embodiments, the distal end of the insert is rounded. In many embodiments, the distal end of the insert has a curved outer boundary. In many embodiments, the distal end of the insert is v-shaped. In many embodiments, the distal end of the insert has a dimpled distal surface. In many embodiments, the first opening or the second opening has a polygonal shape. In many embodiments, the polygonal shape is a triangle, a quadrilateral, a pentagon, a hexagon, an octagon, a nonagon, or a decagon. In many embodiments, at least a portion of an inner surface of the channel comprises threading and at least a portion of an outer surface of the insert body comprises correspondingly-shaped threading such that longitudinal translation of the insert occurs when the insert is rotated relative to the channel. In many embodiments, at least a portion of the inner surface of the channel is not threaded. In many embodiments, the insert body is configured to be press fit into the channel. In many embodiments, the anchor or the insert further comprises a locking mechanism configured to locking the insert in the channel. In many embodiments, the locking mechanism comprises a ratchet, detent, or snap fit. In many embodiments, the anchor body has a circular cross-section. In many embodiments, the anchor body comprises a diameter within a range of about 3 mm to about 6.5 mm. In many embodiments, the anchor body comprises a length between the proximal end and the distal end within a range of about 10 mm to about 30 mm. In many embodiments, the insert body has a circular cross-section. In many embodiments, the insert body comprises a diameter within a range of about 1.8 mm to about 4 mm. In many embodiments, the insert body comprises a length between the proximal end and the distal end within a range of about 4 mm to about 10 mm. In many embodiments, the insert further comprises a device coupler configured to couple the insert to a delivery device. In many embodiments, the device coupler comprises a cavity extending distally from the proximal end of the insert body. In many embodiments, the device coupler comprises a proximal protrusion extending proximally from the proximal end of the insert body. In many embodiments, the system comprises a delivery device comprising a driver configured to couple to a device coupler of the insert. In many embodiments, the delivery device further comprises an inner shaft and wherein the driver is translatably or rotationally disposed within the inner shaft. In many embodiments, the first lateral side comprises a first suture groove extending parallel to the longitudinal axis of the anchor body from the first opening to the proximal end of the anchor body and wherein the second lateral side comprises a second suture groove extending parallel to the longitudinal axis of the anchor body from the second opening to the proximal end of the anchor body. In many embodiments, the proximal end of the anchor body comprises a proximal taper which terminates the first suture groove distal to the proximal end of the anchor body. In many embodiments, the anchor body comprises an interruption which terminates the first suture groove proximal to the first opening. In many embodiments, the first suture groove comprises a proximal step which reduces a depth of the first suture groove at the proximal end of the anchor body. In many embodiments, one or more external retention feature are disposed on an outer surface of the anchor body. In many embodiments, the one or more external retention feature comprises a bump, a ridge, a rib, a thread, a scale, an extension, a protrusion, or a projection. In many embodiments, at least one of the one or more external retention feature is located distal of the first opening and the second opening. In many embodiments, the distal end of the anchor body comprises a distal tip. In many embodiments, the distal tip is pointed, conical, tapered, or blunt. In many embodiments, the anchor comprises polyetheretherketone (PEEK), polylactic acid (PLA), or polyglycolic acid (PGA). In many embodiments, the insert comprises polyetheretherketone (PEEK), polylactic acid (PLA), or polyglycolic acid (PGA). In many embodiments, the system comprises a suture disposed through the suture passage. In many embodiments, at least two sutures are disposed through the suture passage.

Provided herein are methods of anchoring a tissue to bone. An exemplary method comprises a) positioning an anchor into a bone, the anchor comprising: an anchor body having a proximal end, a distal end, a longitudinal axis, a first lateral side extending between the proximal end and the distal end, and a second lateral side extending between the proximal end and the distal end and opposite laterally of the first lateral side, a suture passage comprising a proximal surface and a distal surface and extending through the anchor body from a first opening in the first lateral side to a second opening in the second lateral side, a channel extending along the longitudinal axis of the anchor body from a proximal opening in the proximal end of the anchor body to a distal opening in the proximal surface of the suture passage, wherein the channel does not extend past the distal surface of the suture passage, and a suture disposed through the suture passage; b) passing the suture through or around a tissue to be repaired; c) tensioning the suture to secure the tissue to the bone; d) longitudinally translating the insert within the channel towards the distal surface of the suture passage; and e) compressing the suture between the distal end of the insert and the distal surface of the suture passage, thereby locking the suture in the suture passage. In many embodiments, the distal surface of the suture passage is v-shaped and has a first lateral plane extending from the first opening towards a central normal plane and a second lateral plane extending from the second opening towards the central normal plane, the central normal plane being substantially perpendicular to the longitudinal axis of the anchor body. In many embodiments, the distal surface of the suture passage is substantially flat and substantially perpendicular to the longitudinal axis of the anchor body. In many embodiments, at least a portion of the distal surface of the suture passage comprises a convex curvature extending proximally towards the distal opening of the channel. In many embodiments, a proximal portion of the convex curvature extends into the distal opening of the channel. In many embodiments, the convex curvature spans the entire distal surface. In many embodiments, the distal end of the insert is shaped to correspond to the distal surface of the suture passage. In many embodiments, the distal end of the insert is rounded. In many embodiments, the distal end of the insert has a curved outer boundary. In many embodiments, the distal end of the insert is v-shaped. In many embodiments, the distal end of the insert has a dimpled distal surface. In many embodiments, the first opening or the second opening has a polygonal shape. In many embodiments, at least a portion of an inner surface of the channel comprises threading, wherein at least a portion of an outer surface of the insert body comprises correspondingly-shaped threading, and wherein longitudinally translating the insert comprises rotating the insert relative to the channel. In many embodiments, the insert comprises a device coupler and further comprising coupling the insert to a delivery device with the device coupler. In many embodiments, the device coupler comprises a cavity extending distally from the proximal end of the insert body. In many embodiments, the device coupler comprises a proximal protrusion extending proximally from the proximal end of the insert body. In many embodiments, the method comprises retaining the anchor in the bone with one or more external retention feature disposed on an outer surface of the anchor body. In many embodiments, the one or more external retention feature comprises a bump, a ridge, a rib, a thread, a scale, an extension, a protrusion, or a projection. In many embodiments, positioning the suture anchor comprises driving the suture anchor into the bone without drilling a hole. In many embodiments, positioning the suture anchor comprises inserting the suture anchor into a pre-drilled hole in the bone. In many embodiments, the method comprises drilling the hole in the bone prior to positioning the suture anchor therein. In many embodiments, the method comprises locking the insert in the channel after compressing the suture.

These and other embodiments are described in further detail in the following description related to the appended drawing figures.

BRIEF DESCRIPTION OF THE DRAWINGS

Specific embodiments of the disclosed devices, delivery systems, or methods will now be described with reference to the drawings. Nothing in this detailed description is intended to imply that any particular component, feature, or step is essential to the invention.

FIG. 4A shows a front view, FIG. 4B shows a perspective view, FIG. 4C shows a front view rotated 90° relative to FIG. 4A, and FIG. 4D shows a top view.

FIG. 6C shows a cross-sectional front view of the anchor body, FIG. 6D shows a cross-sectional front view of the suture passage, FIG. 6E shows a top view of the anchor body, and FIG. 6F shows a perspective view of the suture passage.

FIG. 6G shows a cross-sectional front view of the anchor body, FIG. 6H shows a cross-sectional front view of the suture passage, FIG. 6I shows a top view of the anchor body, and FIG. 6J shows a perspective view of the suture passage.

FIG. 7A shows a front view, FIG. 7B shows a top view, FIG. 7C shows a perspective view, FIG. 7D shows a front cross-sectional view taken along line A-A of FIG. 7A, and FIG. 7E shows a front cross-sectional view taken along line B-B of FIG. 7B.

FIG. 8A shows a cross-sectional front view, FIG. 8B shows a top view, and FIG. 8C shows a front view.

FIG. 9A shows a cross-sectional front view, FIG. 9B shows a top view, and FIG. 9C shows a front view.

FIG. 16A shows a perspective view of the distal end of the delivery device coupled to the anchor. FIG. 16B shows a front view of the anchor of FIG. 16A. FIG. 16C shows a perspective view of the distal end of the delivery device coupled to the insert. FIG. 16D shows a top cross-sectional view of the system of FIG. 16B.

FIG. 18B shows the insert in the channel of the anchor body in an unlocked configuration. FIG. 18C shows the system of FIG. 18B further comprising a suture and delivery device driver.

FIG. 19A shows a front view, FIG. 19B shows a top view, FIG. 19C shows a front view rotated 90° relative to FIG. 19A, and FIG. 19D shows a front cross-sectional view.

FIG. 22A shows a front view, FIG. 22B shows an isometric view in the locked configuration, and FIG. 22C shows an isometric view in the unlocked configuration.

FIGS. 23A and 23B show front cross-sectional views of the system of FIGS. 22A-22C in the unlocked and locked configurations, respectively, in accordance with some embodiments.

FIG. 24A shows a front view, FIG. 24B shows an isometric view in the locked configuration, and FIG. 24C shows an isometric view in the unlocked configuration.

FIG. 26A shows a front view, FIG. 26B shows a top view of FIG. 26A, FIG. 26C shows a front view rotated 90° relative to FIG. 26A, FIG. 26D shows a top view of FIG. 26C, and FIG. 26E shows a front view rotated 180° relative to FIG. 26A.

FIG. 27A shows a front-cross-sectional view taken along line B-B of FIG. 26E. FIG. 27B shows a front-cross-sectional view taken along line A-A of FIG. 27A. FIG. 27C shows a front cross-sectional view of the anchor with an insert locking a suture therein. FIG. 27D shows a front cross-sectional view of the suture passage of FIG. 27C.

FIG. 28A shows a cross-sectional front view of the anchor body, FIG. 28B shows a cross-sectional front view of the suture passage, FIG. 28C shows a top view of the anchor body, and FIG. 28D shows a perspective view of the suture passage.

FIG. 29A shows a cross-sectional front view of the anchor body, FIG. 29B shows a cross-sectional front view of the suture passage, FIG. 29C shows a top view of the anchor body, and FIG. 29D shows a perspective view of the suture passage.

FIG. 31A shows a perspective view, FIG. 31B shows a front view, and FIG. 31C shows a top view.

FIG. 32A shows a perspective view of the anchor body, FIG. 32B shows a front view of the anchor body, FIG. 32C shows a top view of the anchor body, and FIG. 32D shows a front view of the suture passage.

FIG. 33A shows a perspective view, FIG. 33B shows a front view, and FIG. 33C shows a top view.

DETAILED DESCRIPTION

Specific embodiments of the disclosed device and method of use will now be described with reference to the drawings. Nothing in this detailed description is intended to imply that any particular component, feature, or step is essential to the invention.

It would be desirable to provide improved knotless suture anchor devices and methods that overcome some of the challenges of existing devices. For example, it would be desirable to provide a knotless suture anchor device that locks into place on the suture material while maintaining the integrity of the suture material. Additionally, it would be desirable to provide a knotless suture anchor that may be used to secure soft tissue that is engaged by the suture material. The embodiments described herein address at least some of these challenges and benefits.

Devices and methods as disclosed herein provide a suture anchor that may be used to fixate soft tissue to bone. Suture anchors as described herein may be used for surgeries such as labral repair, muscle repair, tendon repair, and ligament repair, in addition to other examples of surgery. In some embodiments, suture anchors as provided herein may be used in surgery by first drilling a pilot hole into a bone of a patient; inserting the suture anchor into the bone; passing suture material from the suture anchor around soft tissue; providing tension to the suture material to hold the tissue again a corresponding bone; and locking the suture into place by compressing an insertion member to engage the suture material while preserving the integrity of the suture material.

Figure 1:
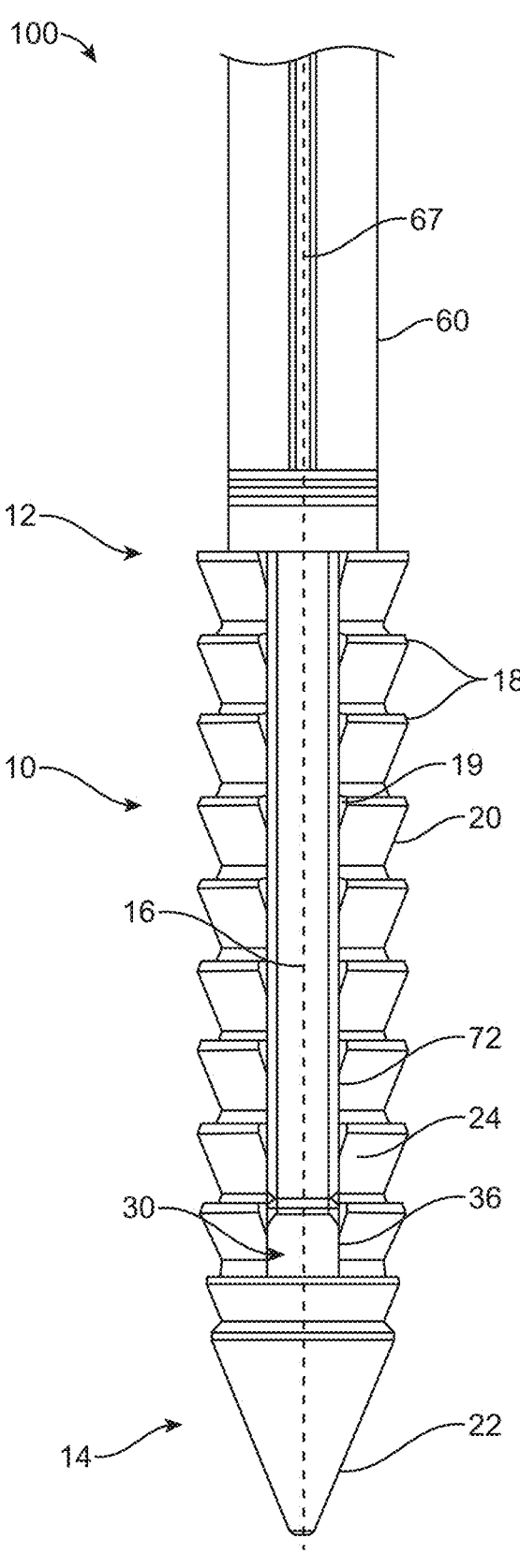
FIG. 1 shows a front view of an anchor system coupled to a delivery device, in accordance with some embodiments.
Figure 2:
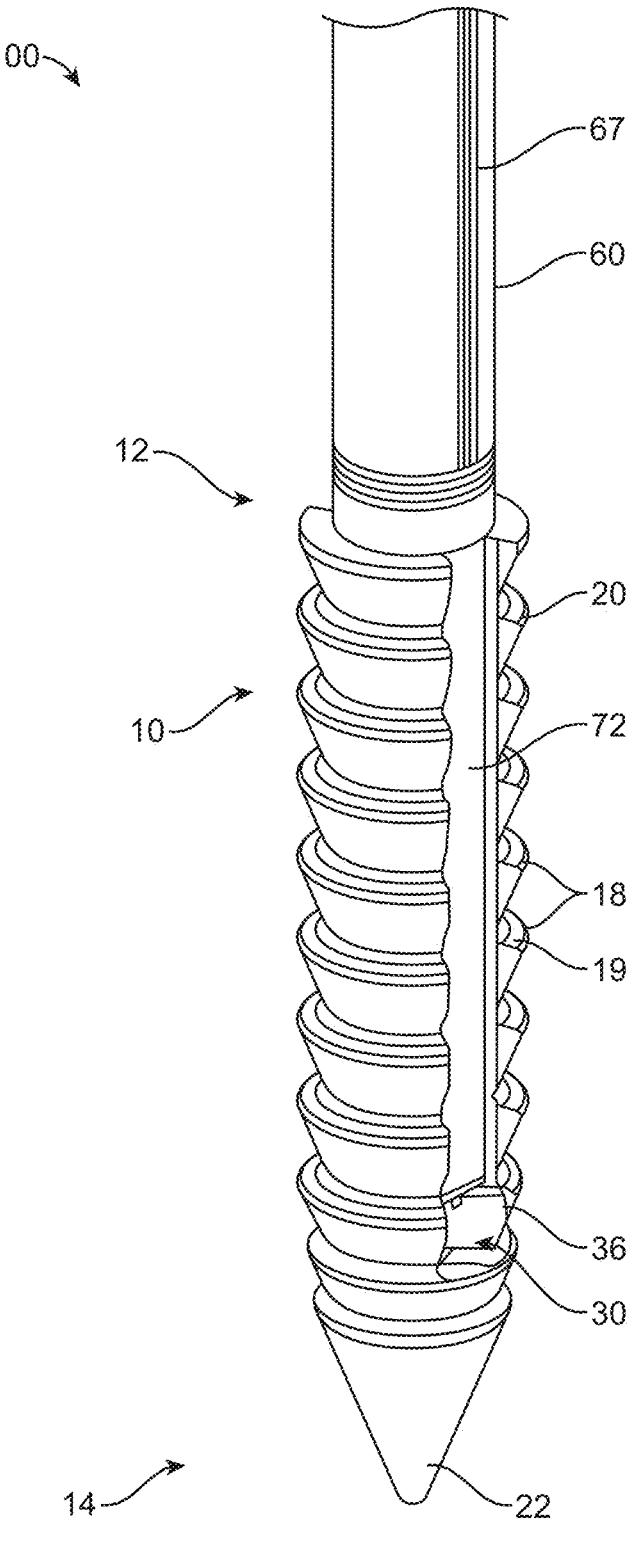
FIG. 2 shows a perspective view of the system of FIG. 1, in accordance with some embodiments.

FIG. 1 shows a front view of an anchor system 100 comprising an anchor 10 coupled to a delivery device 60. FIG. 2 shows a perspective view of the system 100. The anchor 10 comprises an anchor body 20 having a proximal end 12, a distal end 14, a first lateral side 24 extending between the proximal end 12 and the distal end 14, and a second lateral side (e.g., second lateral side 26 shown in FIG. 4A) extending between the proximal end 12 and the distal end 14 opposite laterally of the first lateral side 24. A first opening 36 is disposed in the first lateral side 24. A suture passage 30 extends through the anchor body 20 from the first opening 36 to a second opening (e.g., second opening 38 shown in FIG. 5A) in the second lateral side. An optional suture groove 72 runs parallel to the longitudinal axis 16 of the anchor body 20 and extends from the first opening 36 to the proximal end 12. The distal end 14 comprises a distal tip 22.

In some embodiments, one or more external retention features 18 are disposed on an outer surface of the anchor body 20 to enhance friction or to mechanically enhance retention of the anchor 10 within the bone. The suture groove 72 (and other suture grooves described herein, e.g., suture groove 74) may be recessed relative to the one or more external retention features 18 to ensure that a suture disposed therealong does not protrude outward past the external retention feature(s) 18 to contact the bone. By providing sufficient space to avoid the suture contacting bone, the suture groove 72 may enable sliding of the suture within the suture groove 72 (and suture passage 30, and other grooves described herein) and adjustment of suture tension after the anchor 10 has been positioned in the bone but before the suture has been locked within the suture passage 30 as described herein. The one or more external retention features 18 may further comprise relief(s) 19 adjacent the suture groove 72 to blunt the portion of the external retention feature(s) 18 directly adjacent the suture to prevent damage to the suture which may otherwise occur in at least some instances when the external retention feature(s) 18 have sharp edges adjacent the suture. In some embodiments, at least one of the one or more external retention features 18 is disposed distal to the opening(s) (e.g., first opening 36 and/or second opening 38 shown in FIG. 5A) to the suture passage 30.

The one or more external retention features 18 may comprise bumps, ridges, ribs, threads, scales, extensions, protrusions, projections, or the like, or any combination thereof.

Figure 3:
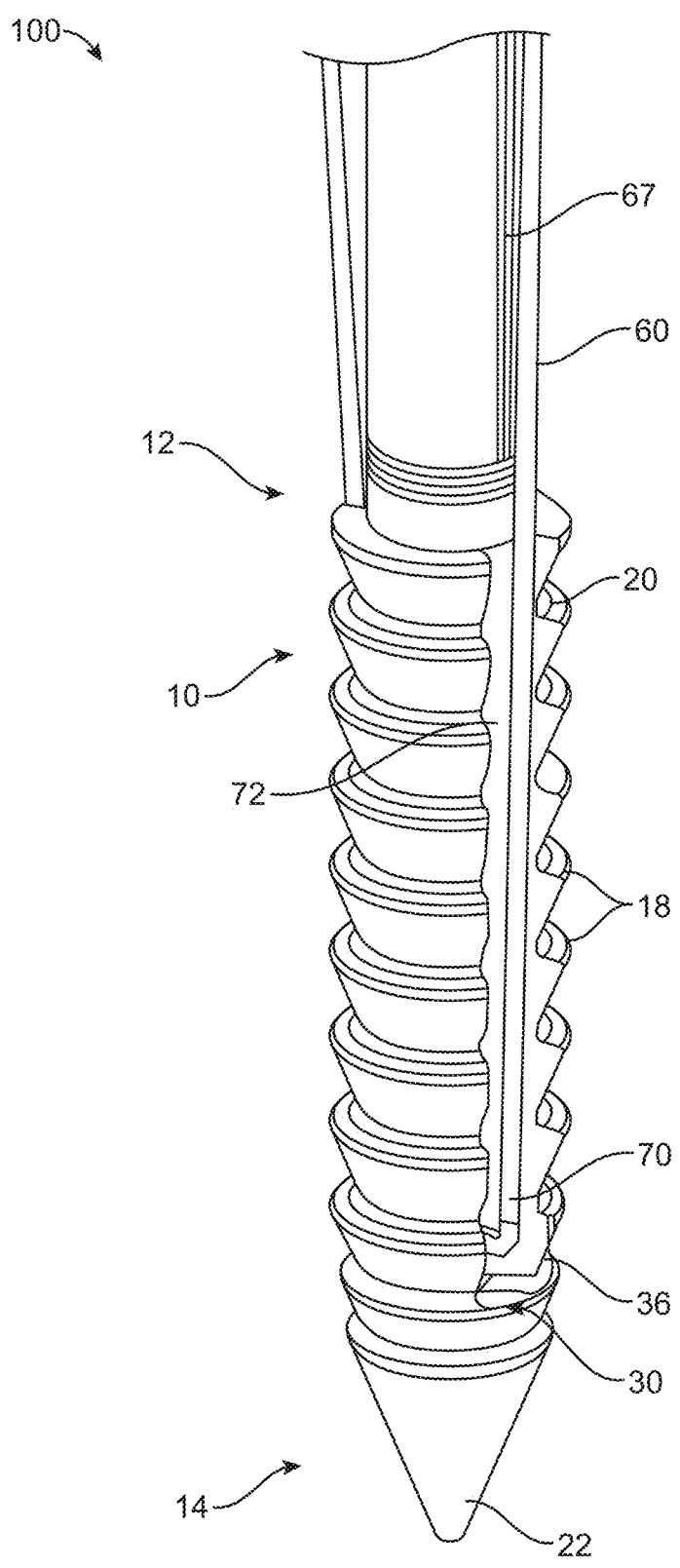
FIG. 3 shows an isometric view of the system of FIG. 1 including a suture disposed within the suture passage, in accordance with some embodiments.

In some embodiments, the delivery device 60 comprises one or more alignment markings 67 disposed thereon. The alignment marking 67 may be used to align the delivery device 60, and therefore the anchor body 20, to a desired position within a bone such that a suture (e.g., suture 70 as shown in FIG. 3) aligns as desired with respect to a portion of soft tissue for repair. The anchor body 20 and the delivery device 60 are shown in a delivery configuration with the alignment markings 67 aligned to the suture groove 72.

The distal tip 22 may be conical (as shown), pointed, tapered, blunt, or the like as will be understood by one of ordinary skill in the art based on the teachings herein.

In some embodiments, the first opening 36 (and second opening 38 shown in FIG. 5A) has a polygonal cross-section. The suture passage 30 may also have a polygonal cross-section. In some embodiments, the first opening 36 (and second opening 38 shown in FIG. 5A) has a square cross-section. The suture passage 30 may also have a square cross-section. In some embodiments, the first opening 36 (and second opening 38 shown in FIG. 5A) has a rectangular cross-section. The suture passage 30 may also have a rectangular cross-section. In some embodiments, the polygonal cross-section is triangular, quadrilateral (e.g., square or rectangular), pentagonal, hexagonal, octagonal, nonagonal, decagonal, or any other cross-section desired by one of ordinary skill in the art.

In some embodiments, the first opening 36 (and second opening 38 shown in FIG. 5A) has cross-section that is asymmetrical, circular, or curved.

In some embodiments, the first opening 36 (and second opening 38 shown in FIG. 5A) has a width within a range of about 1 mm to about 3 mm, such as about 1.2 mm to about 2.5 mm. For example, the width may be within a range of about 1.5 mm to about 2 mm.

In some embodiments, the first opening 36 (and second opening 38 shown in FIG. 5A) has a height within a range of about 1 mm to about 4 mm, such as about 1.2 mm to about 2.5 mm. For example, the height may be within a range of about 1.5 mm to about 2 mm.

In some embodiments, the suture passage 30 has a width within a range of about 1 mm to about 3 mm, such as about 1.2 mm to about 2.5 mm. For example, the width may be within a range of about 1.5 mm to about 2 mm.

In some embodiments, the suture passage 30 has a height within a range of about 1 mm to about 3 mm, such as about 1.2 mm to about 2.5 mm. For example, the height may be within a range of about 1.5 mm to about 2 mm.

In some embodiments, the anchor body 20 has a length between the proximal end 12 and the distal end 14 within a range of about 10 mm to about 30 mm, such as about 12 mm to about 25 mm. For example, the anchor body 20 may be about 21 mm long.

In some embodiments, the anchor body 20 comprises a radiolucent material, such as polyetheretherketone (PEEK). In some embodiments, the anchor body 20 comprises a biocomposite or bioabsorbable material, such as polylactic acid (PLLA). In some embodiments, the anchor body 20 comprises a biodegradable material, such as polyglycolic acid (PGA). In some embodiments, the anchor body 20 comprises a combination of materials. In some embodiments, one or more of the materials may be radiopaque. For example, the anchor body 20 may comprise radiopaque PEEK (non-translucent).

Figures 4A, 4B, 4C, 4D:
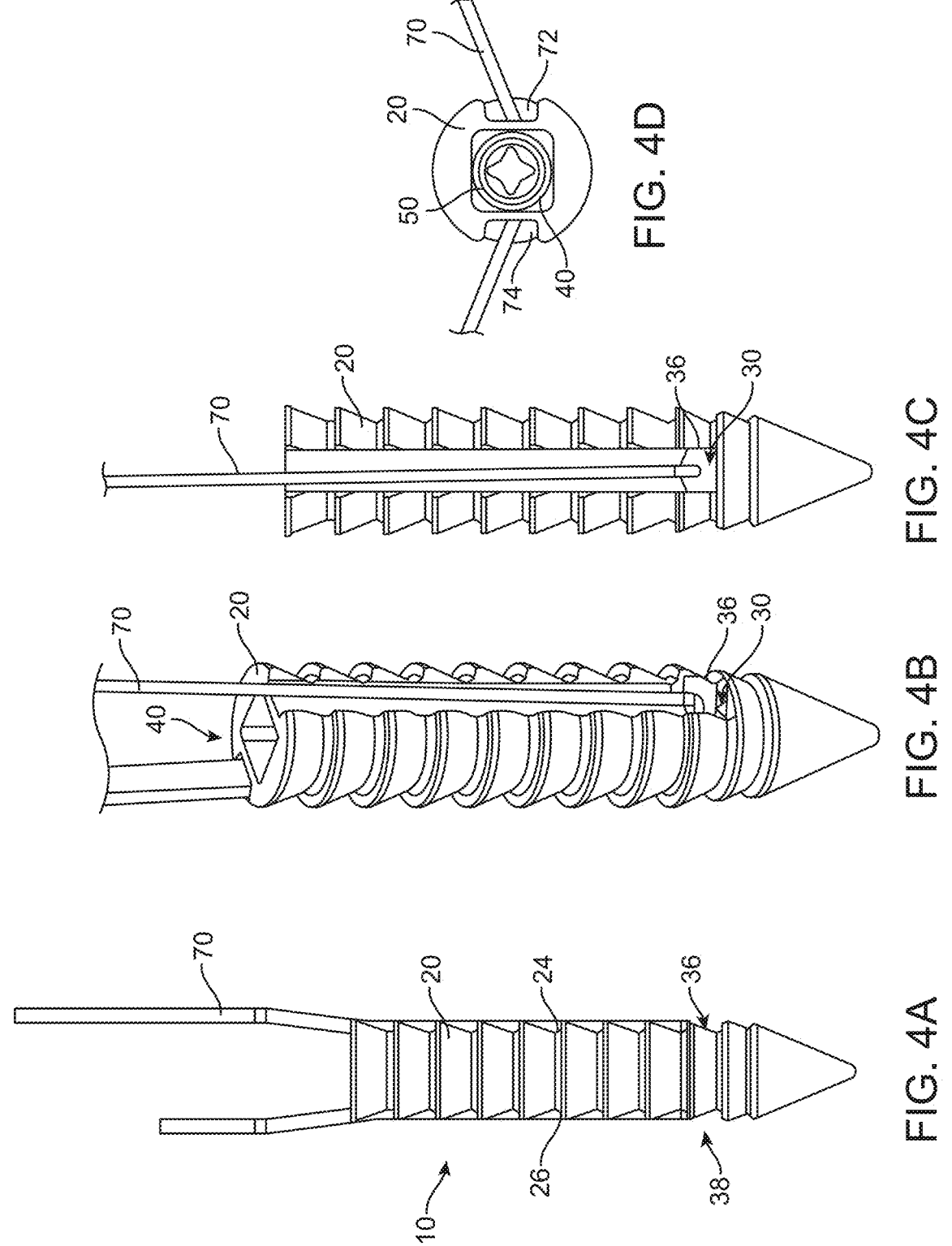
FIGS. 4A-4D show various external views of the system of FIG. 3 without the delivery device, in accordance with some embodiments.

FIG. 3 shows an isometric view of the system 100 of FIG. 1 including a suture 70 disposed within the suture passage 30. FIGS. 4A-4D show various external views of the system of FIG. 3 without the delivery device 60. FIG. 4A shows a front view, FIG. 4B shows a perspective view, FIG. 4C shows a front view rotated 90° relative to FIG. 4A, and FIG. 4D shows a top view including insert 50 within a channel 40 of the anchor body 20. The suture 70 is shown disposed within the suture passage 30 with a first end extending proximally out of the first opening 36 and along the first suture groove 72 and a second end extending proximally out of the second opening 38 in the second lateral side 26 of the anchor body 20 and along the second suture groove 74 running parallel to the longitudinal axis 16 of the anchor body 20 and extending from the second opening 38 to the proximal end 12. The suture 70 is recessed relative to the one or more external retention features 18 to ensure that the suture 70 disposed therealong does not protrude outward past the external retention feature(s) 18 to contact the bone when the anchor is inserted therein. The recessed suture 70 can slide freely within the suture passage 30 and along the first and second suture grooves 72, 74 which allows for adjustment of suture tension after the anchor 10 has been positioned in the bone but before the suture 70 has been locked within the suture passage 30 as described herein.

In some embodiments, the anchor body 20 has a circular cross-section as shown in FIG. 4D.

In some embodiments, the anchor body 20 has an outer diameter within a range of about 3 mm to about 6.5 mm, such as about 3.5 mm to about 6.5 mm. For example, the anchor body 20 may have an outer diameter of about 3.5 mm, about 4.5 mm, or about 5.5 mm.

In some embodiments, the suture 70 comprises a #2 UHMWPE braided suture. In some embodiments, the suture 70 comprises a suture tape. In some embodiments, the suture 70 comprises a flat braid configuration. In some embodiments, the suture 70 comprises a round to flat braid configuration.

In some embodiments, the suture 70 is made from other non-absorbable suture materials, such as polyester. In some embodiments, the suture 70 may be made from an absorbable suture material, such as polyglactin (PGLA). In some embodiments, the suture 70 has a tapered tail for ease of passing through the body.

Figures 5A, 5B:
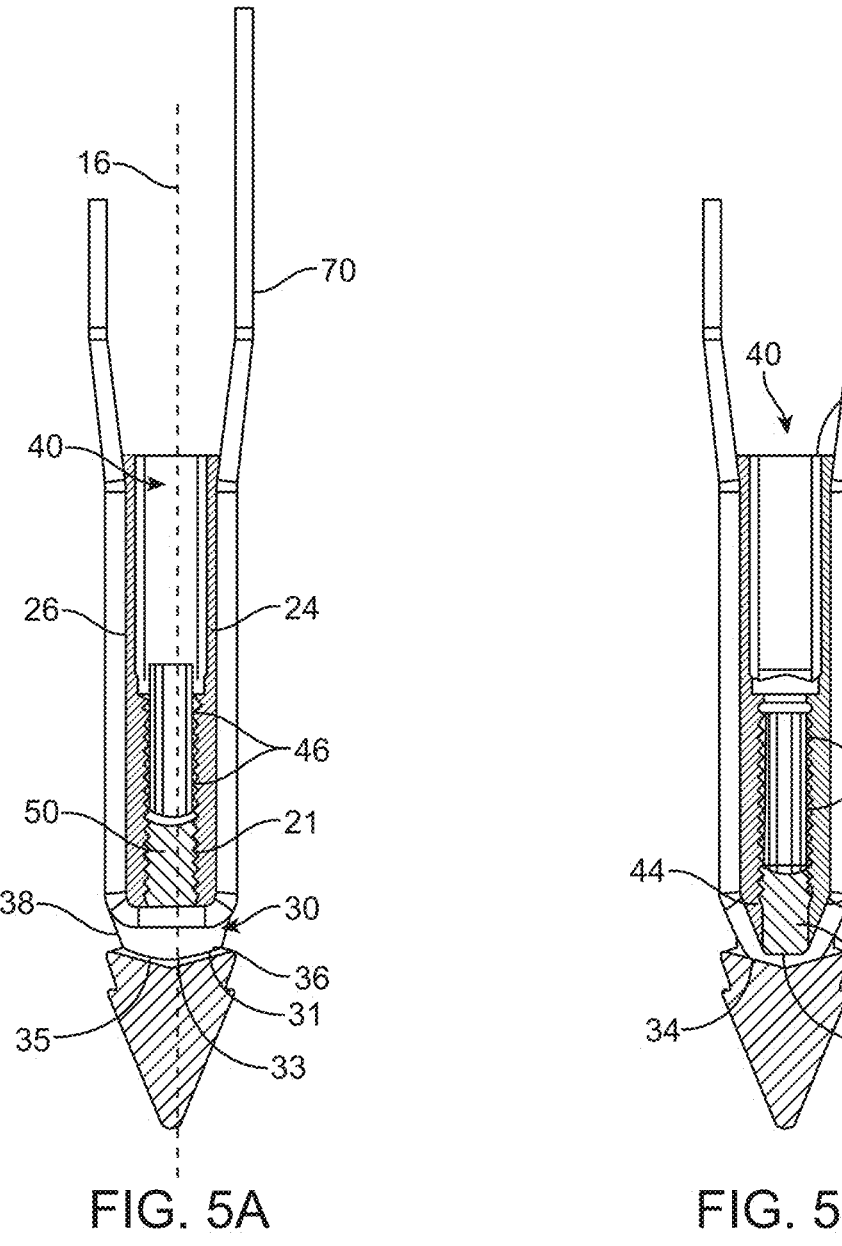
FIGS. 5A and 5B show cross-sectional front views of a suture unlocked and locked by an insert within an anchor body, respectively, in accordance with some embodiments.
Figure 5C:
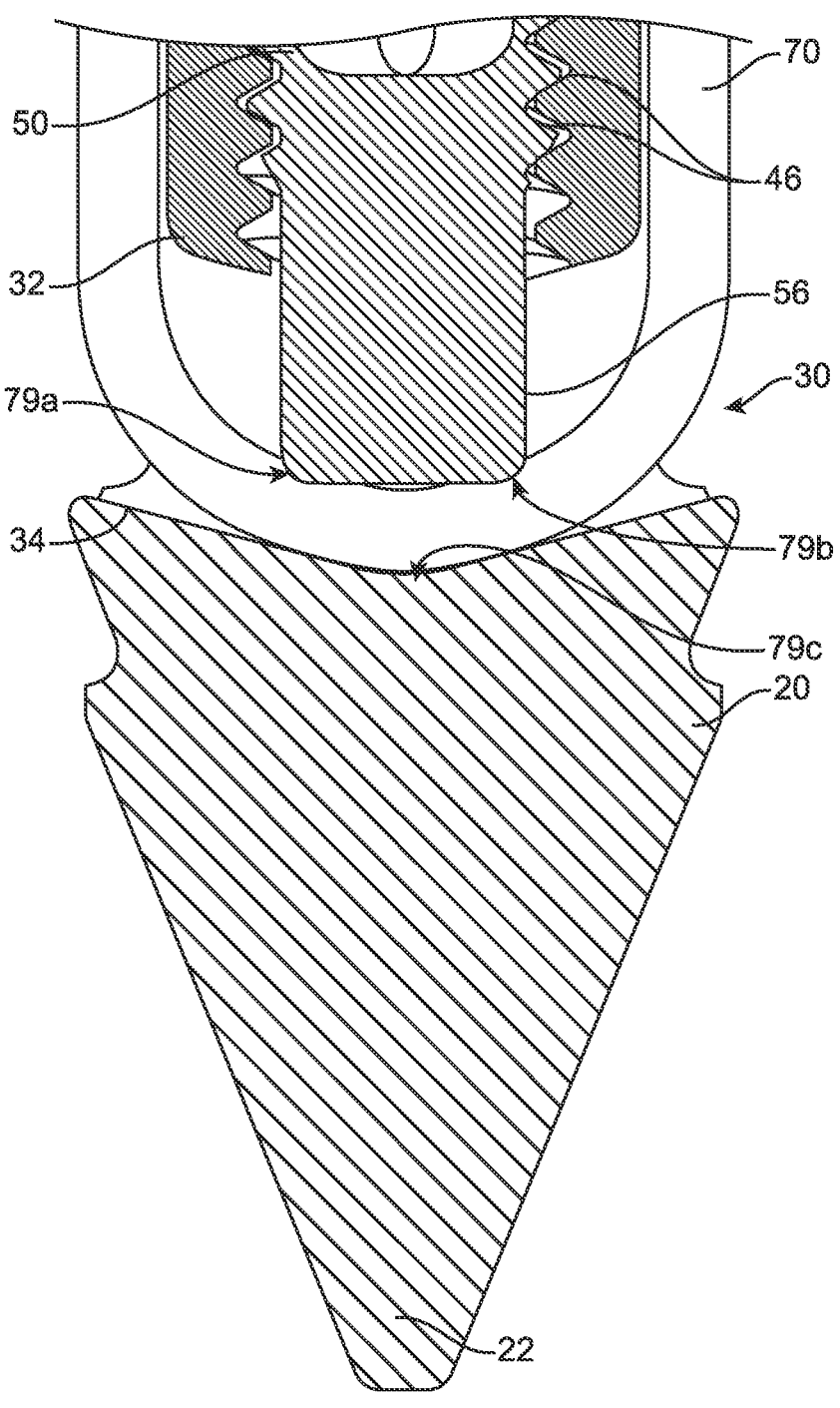
FIG. 5C shows a cross-sectional front view of a suture locked by an insert within the suture passage of the anchor body of FIGS. 5A and 5B, in accordance with some embodiments.

FIGS. 5A-5C show cross-sectional front views of a suture 70 unlocked and locked by an insert 50 within an anchor 10, respectively. The anchor 10 may be substantially similar to any of the anchors described herein. FIG. 5A shows the insert 50 in an unlocked configuration. FIG. 5B shows the insert 50 in a locked configuration. FIG. 5C shows an enlarged view of the insert 50 compressing the suture 70 within the suture passage 30 with the insert 50 in the locked configuration. The suture passage 30 comprises a proximal surface 32 and a distal surface 34. The insert 50 is disposed within a channel 40 extending along the longitudinal axis 16 of the anchor body 20 from a proximal opening 42 to a distal opening 44 in the proximal surface 32 of the suture passage 30. Longitudinal translation of the insert 50 within the channel 40 towards the distal surface 34 of the suture passage 30 from the unlocked configuration to the locked configuration compresses the suture 70 between the distal end 56 of the insert 50 and the distal surface 34 of the suture passage 30 in order to secure the suture 70 in the suture passage 30 as described herein.

The distal surface 34 of the suture passage 30 is optionally v-shaped. The v-shaped distal surface 34 can comprise a first lateral plane 31 extending at an angle from the first opening 36 toward a central normal plane 33 and a second lateral plane 35 extending at an angle from the second opening 38 toward the central normal plane 33. The central normal plane 33 is substantially perpendicular to the longitudinal axis 16 of the anchor body 20. In some embodiments, there is no central normal plane 33 and the first and second lateral planes 31, 35 come together at a point or curved junction. The v-shaped distal surface 34 provides a surface without sharp edges and therefore enables distribution of forces along a length of the suture 70 instead of concentrated pressure points (which occur with sharp edges) when the insert 50 is in the locked configuration. In at least some instances, spreading the forces over a length of the suture will benefit suture integrity, enabling better locking, less strain on the suture, and reduced risk to patients that the suture will fail after implantation.

In some embodiments, three or more points of capture of the suture 70 exist within the suture passage 30. For example, when the distal surface 34 of the suture passage 30 is v-shaped, the suture 70 is captured by at least a first capture point 79a, a second capture point 79b, and a third capture point 79c. The first capture point 79a may be between the suture 70 and a first lateral side of the distal end 56 of the insert 50. The second capture point 79b may be between the suture 70 and a second lateral side of the distal end 56 of the insert 50. The third capture point 79c may be between the distal end 56 of the insert 50 and the distal surface 34 of the suture passage 30. In some embodiments, for example, when the suture 70 does not contact the central normal plane 33 of the distal surface 34 of the suture passage 30, the suture 70 may contact one or more of the first lateral plane 31 or the second lateral plane 35 at one or more capture points. In at least some instances, providing three or more capture points will increase the pull-out force necessary to dislodge the suture 70 and provide better securing of the suture 70 after implantation.

The first lateral plane 31 may extend from the first opening 36 towards the central normal plane 33 at an angle relative to the longitudinal axis 16 within a range of about 30° to about 80°.

The second lateral plane 35 may extend from the second opening 38 towards the central normal plane 33 at an angle relative to the longitudinal axis 16 within a range of about 30° to about 80°.

Figure 30:
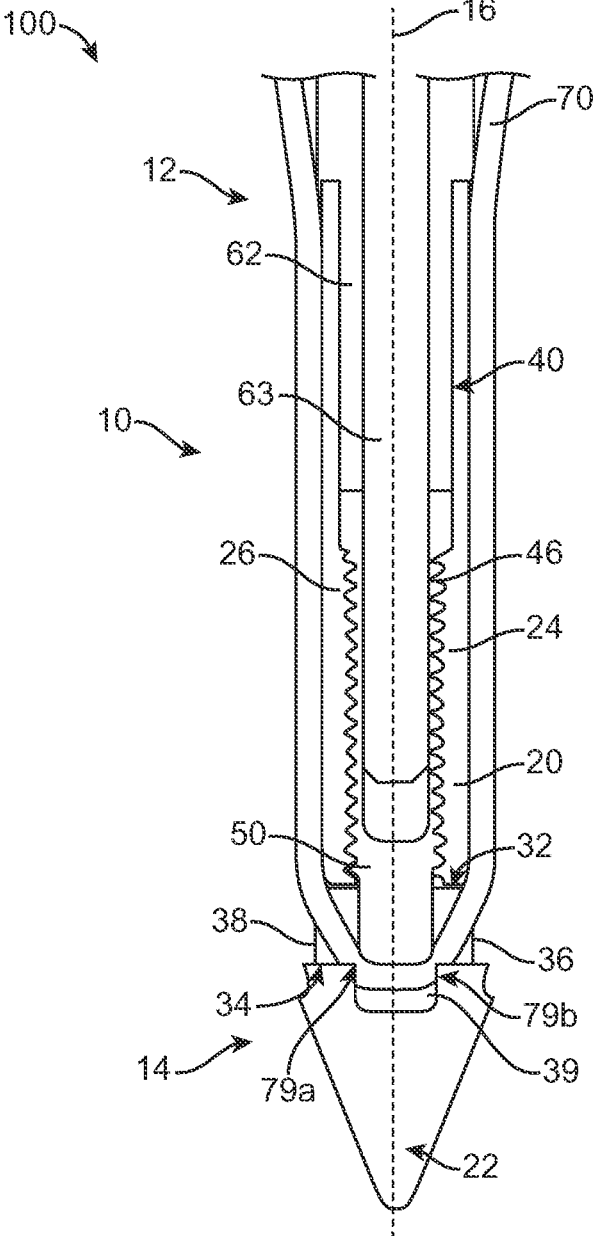
FIG. 30 shows a cross-sectional front view of another anchor system, in accordance with some embodiments.

In some embodiments, the channel 40 opens into the suture passage 30 and does not extend past the distal surface 34 of the suture passage 30. In some embodiments, for example as shown in FIG. 30, the distal surface 34 comprises a pocket 39 which extends the channel 40 distally beyond the distal surface 34 of the suture passage 30.

In some embodiments, at least a portion of an inner surface of the channel 40 comprises threading 46. In some embodiments, a portion of the inner surface of the channel 40 comprises threading 46 and a portion of the inner surface of the channel 40 (e.g., a proximal portion as shown) is not threaded. The insert 50 may comprise corresponding threading (e.g., threading 53 shown in FIG. 7A)

Figures 17A, 17B:
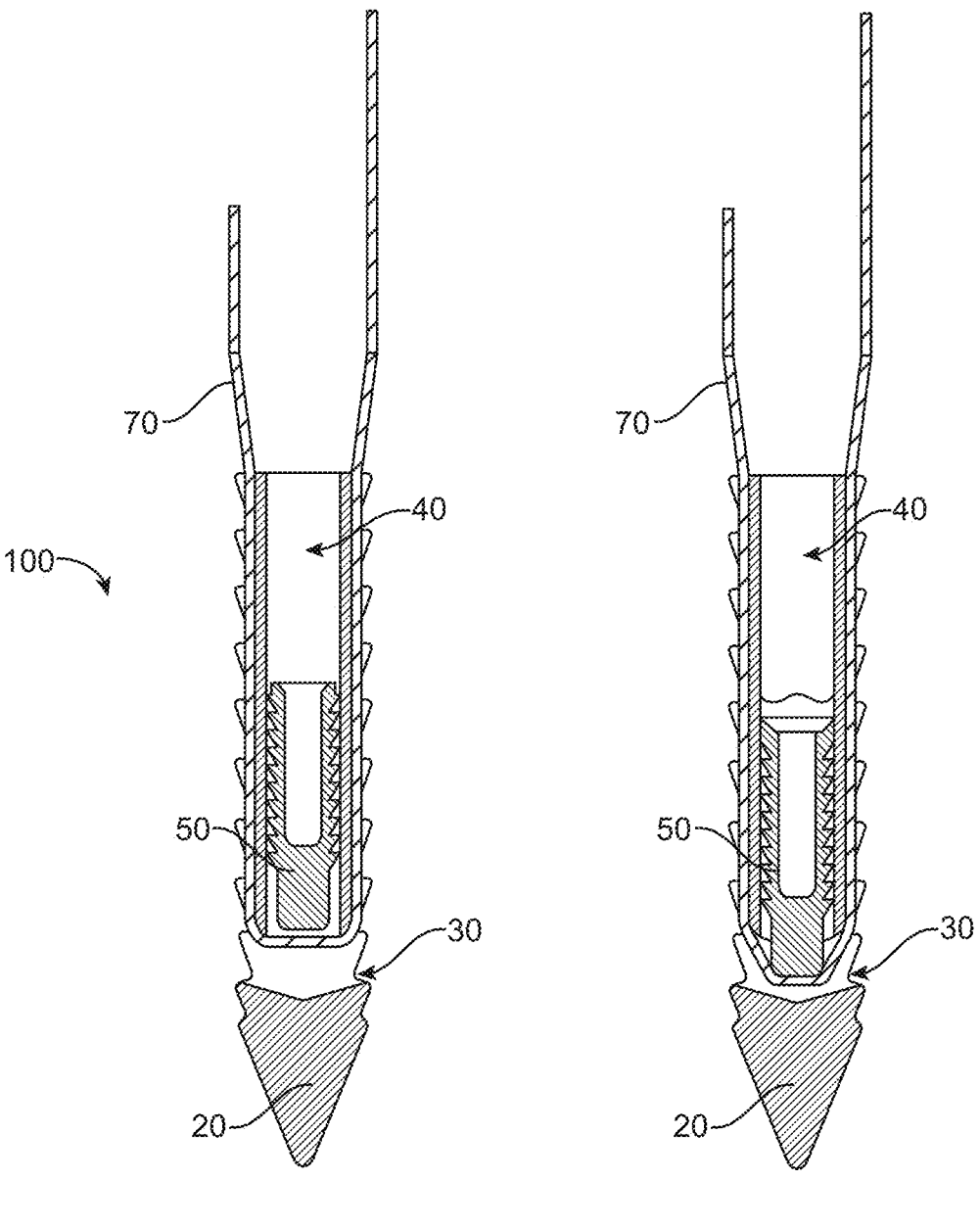
FIGS. 17A and 17B show front cross-sectional views of an anchor system in unlocked and locked configurations, respectively, in accordance with some embodiments.

In some embodiments, the inner surface of the channel 40 is not threaded (e.g., as shown in FIGS. 17A and 17B).

In some embodiments, one or both of the anchor body 20 or the insert 50 comprises a locking mechanism configured to lock the insert 50 in the channel 40. The locking mechanism optionally comprises a ratchet, a detent, a press fit, a snap fit, or the like as will be understood by one of ordinary skill in the art based on the teachings herein. In some embodiments, the threading 46, 53 act as a locking mechanism.

Figure 6A:
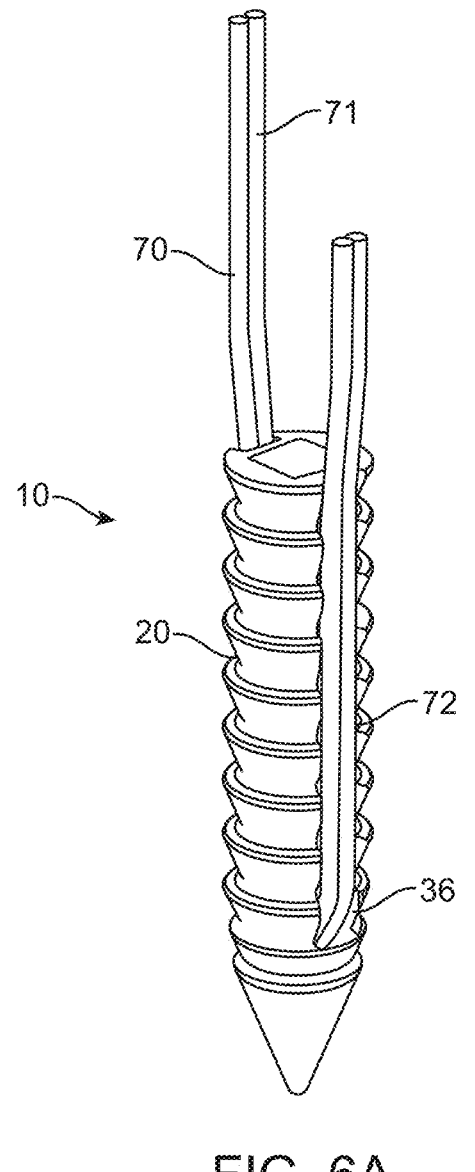
FIGS. 6A and 6B show isometric views of two sutures locked and unlocked, respectively, within an anchor body, in accordance with some embodiments.
Figure 6B:
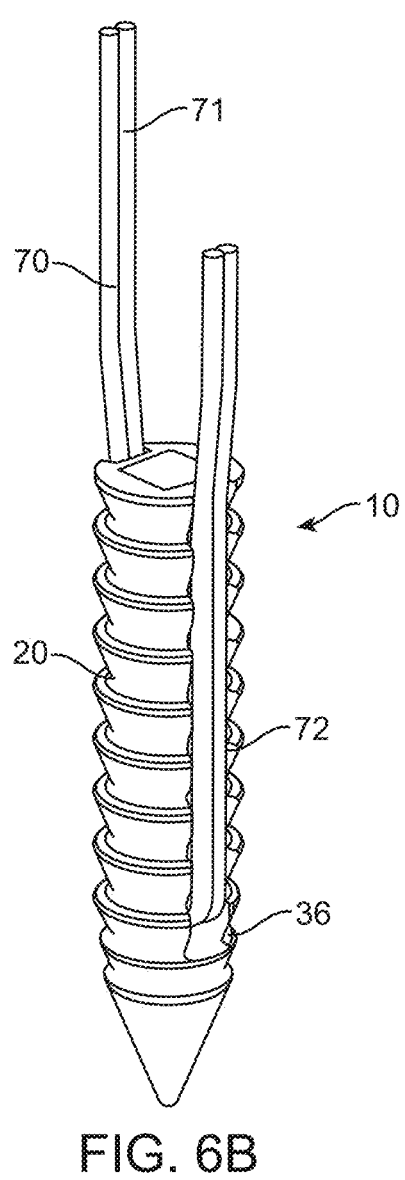

FIGS. 6A and 6B show isometric views of two sutures 70, 71 locked and unlocked, respectively, within an anchor body 20. As will be understood by one of ordinary skill in the art based on the teachings herein, one or more sutures may be disposed within the suture passage 30 and suture grooves 72, 74 of the anchors 10 described herein. For example, one, two, three, or four sutures may be disposed within the suture passage 30. In at least some instances, the use of two or more sutures may add strength and/or reduce the risk of suture failure compared to a single suture alone. The number of sutures may be selected based on the surgical method (e.g., the size of a rotator tear can determine the number of anchors and sutures used whereas a bicep tendon repair typically only has two tails (one suture) which wrap around the tendon), physiology, and/or surgeon preference.

Figures 6C, 6D, 6E, 6F:
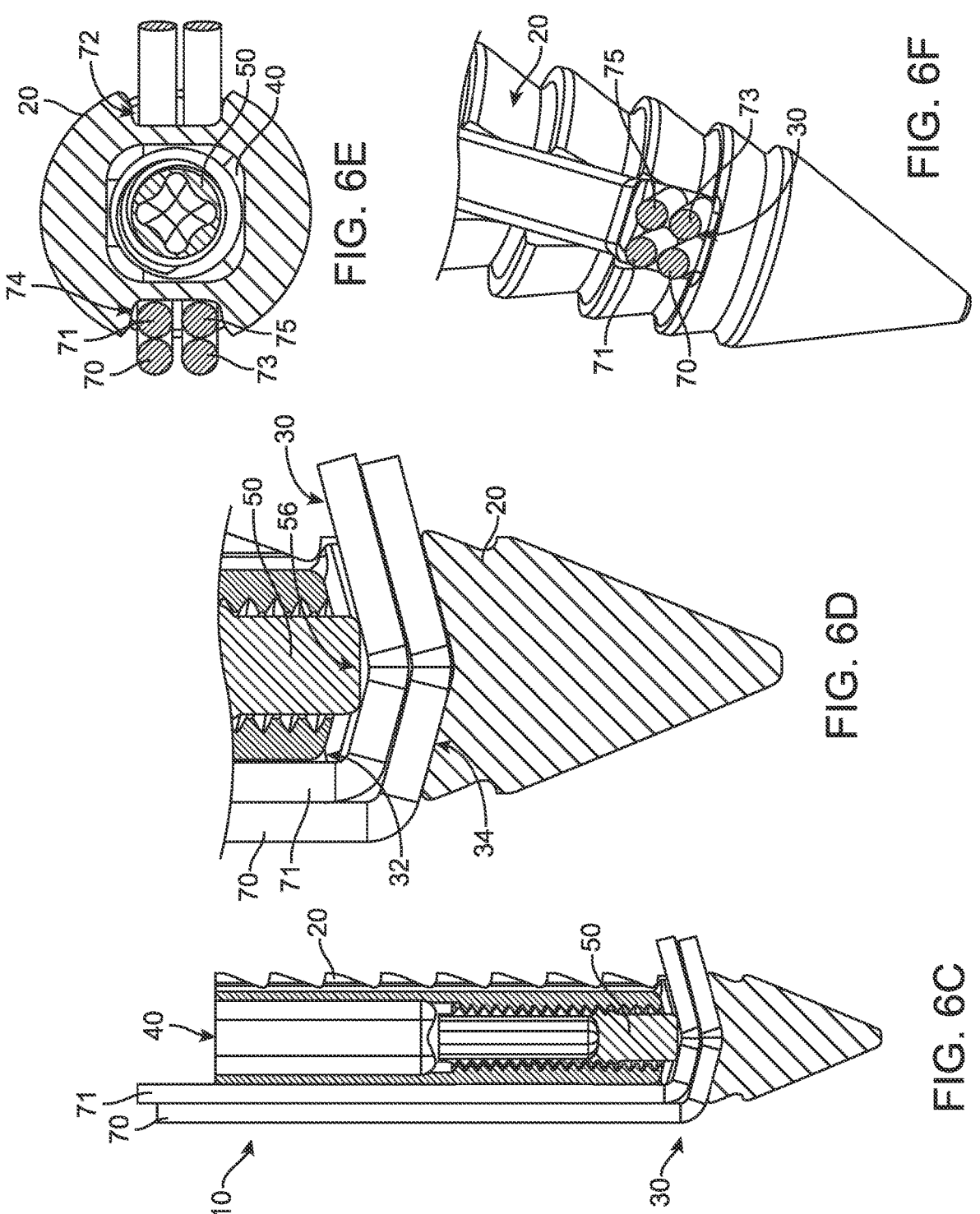
FIGS. 6C-6F show various views of four sutures locked within an anchor body, in accordance with some embodiments.

FIGS. 6C-6F show various views of four sutures 70, 71, 73, 75 locked within an anchor body 20. FIG. 6C shows a cross-sectional front view of the anchor body 20. FIG. 6D shows a cross-sectional front view of the suture passage 30. FIG. 6E shows a top view of the anchor body 20. FIG. 6F shows a perspective view of the suture passage 30. As will be understood by one of ordinary skill in the art based on the teachings herein, one or more sutures (or suture tapes) may be disposed within the suture passage 30 and suture grooves 72, 74 of the anchors 10 described herein. For example, four or more sutures may be disposed within the suture passage 30. The four sutures 70, 71, 73, 75 may be disposed within the suture passage 30 such that two sutures lie on top of the other two sutures. For example, the second suture 71 may be stacked above the first suture 70 and the fourth suture 75 may sit above the third suture 73. The two pairs of sutures may sit side by side within the suture passage 30. The stacked suture pairs can be locked between the distal surface 34 of the suture passage 30 and the distal end 56 of the insert 50 as described herein. The stacked suture pairs may substantially fill the suture passage 30. Even in the locked position, the stacked suture pairs may prevent the insert 50 from blocking the first and second openings of the suture passage 30 and/or from entering the suture passage 30 entirely. In some embodiments, each suture groove 72, 74 is at least two suture widths wide and at least one suture width deep. In some embodiments, each suture groove 72, 74 is at least one suture tape wide and at least one suture tape deep.

Figures 6G, 6H, 6I, 6J:
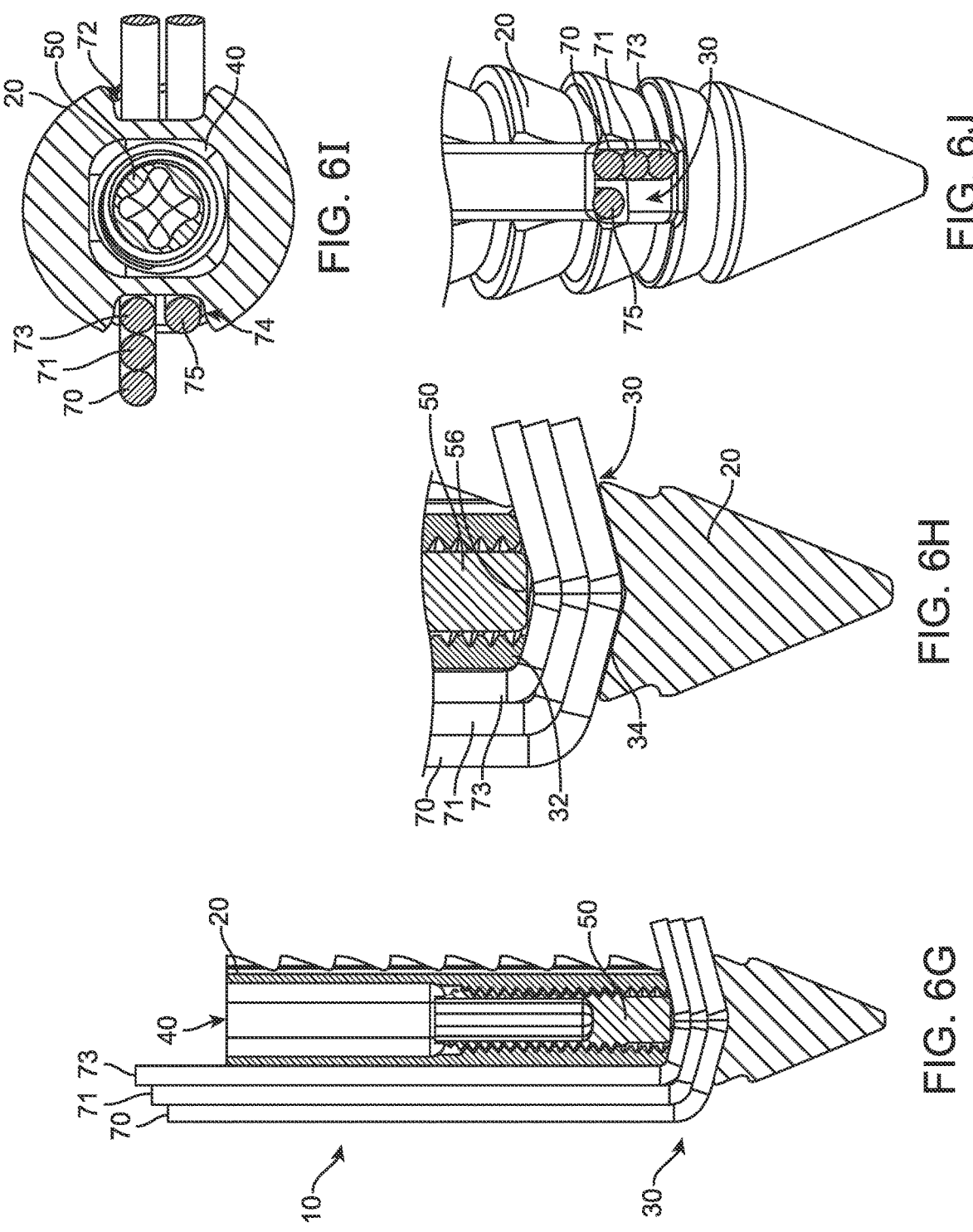
FIGS. 6G-6J show various views of four sutures locked within an anchor body, in accordance with some embodiments.

FIGS. 6G-6J show various views of four sutures 70, 71, 73, 75 locked within an anchor body 20. FIG. 6G shows a cross-sectional front view of the anchor body 20. FIG. 6H shows a cross-sectional front view of the suture passage 30. FIG. 6I shows a top view of the anchor body 20. FIG. 6J shows a perspective view of the suture passage 30. FIGS. 6G-6J are substantially similar to FIGS. 6C-6F except that the first suture 70, second suture 71, and third suture 73 are stacked together within the suture passage 30 while the fourth suture 75 is disposed next to the stack of sutures 70, 71, 73 within the suture passage 30.

Figures 7A, 7B, 7C, 7D, 7E:
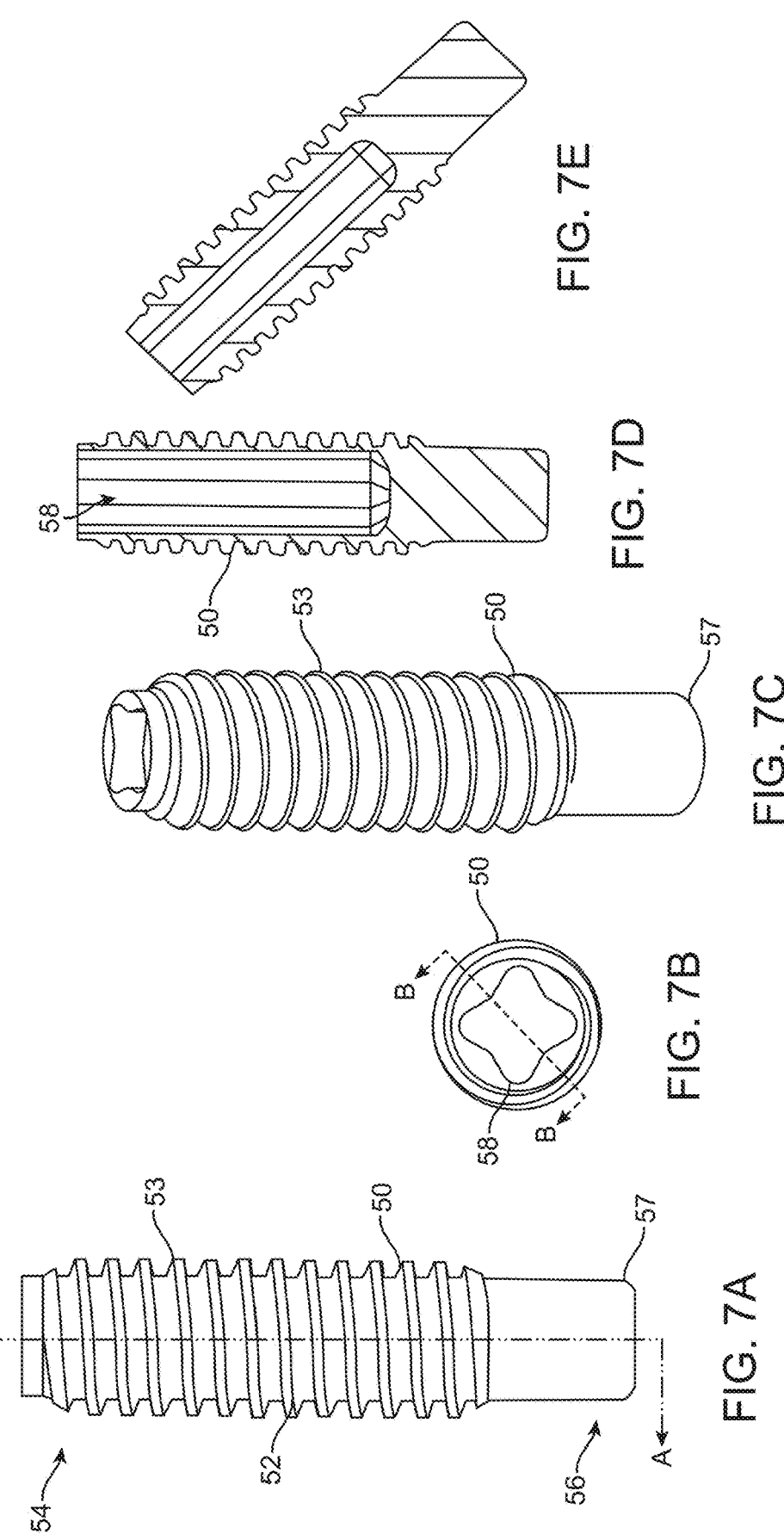
FIGS. 7A-7E shows various views of an insert, in accordance with some embodiments.

FIGS. 7A-7E shows various views of an insert 50. FIG. 7A shows a front view, FIG. 7B shows a top view, FIG. 7C shows a perspective view, FIG. 7D shows a front cross-sectional view taken along line A-A of FIG. 7A, and FIG. 7E shows a front cross-sectional view taken along line B-B of FIG. 7B. The insert 50 comprises an insert body 52 having a proximal end 54 and a distal end 56. The insert 50 is configured to translate longitudinally within a channel (e.g., channel 40 shown in FIG. 5A) of an anchor body (e.g., anchor body 20 shown in FIG. 5A) between a proximal end of the anchor body and a distal surface of a suture passage (e.g., suture passage 30 shown in FIG. 5A). At least a portion of an outer surface of the insert body 52 comprises threading 53 shaped to correspond to threading (e.g., threading 46 shown in FIG. 5A) in the channel. Longitudinal translation of the insert 50 within the channel may occur when the insert 50 is rotated relative to the channel as described herein.

Figure 10:
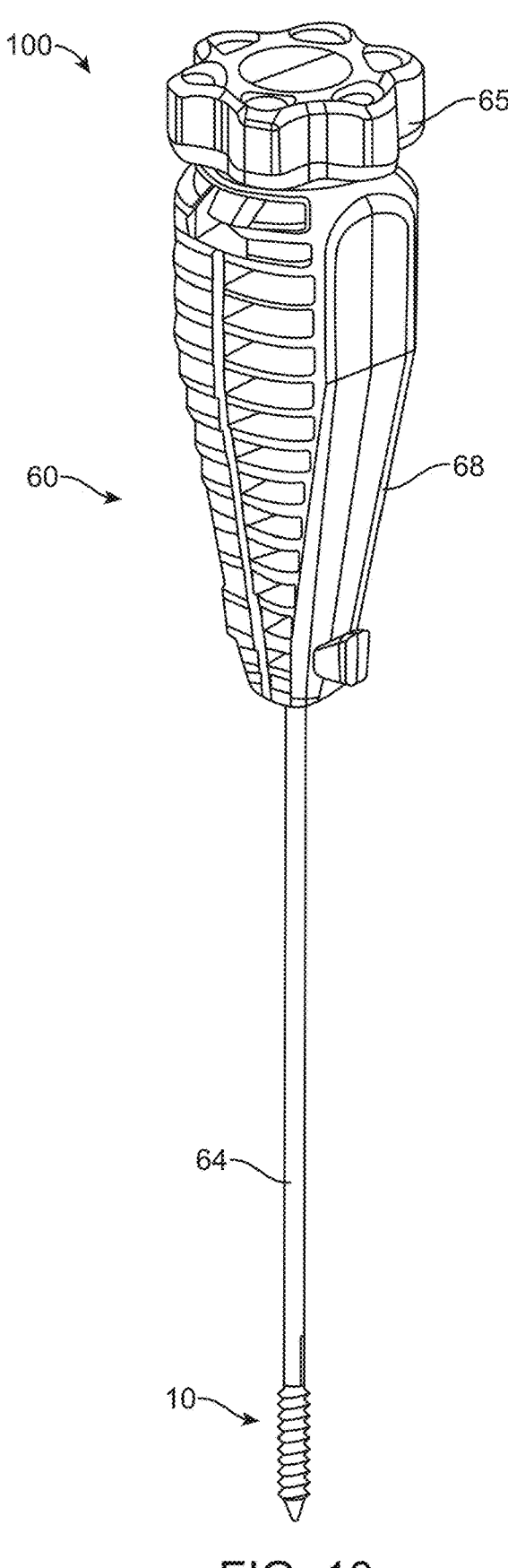
FIG. 10 shows a perspective view of a system comprising a delivery device, an anchor, and an insert, in accordance with some embodiments.

The insert 50 comprises a device coupler 58 configured to couple the insert 50 to a delivery device (e.g., delivery device 60 shown in FIG. 10). The device coupler 58 optionally comprises a cavity extending distally from the proximal end 54 of the insert body 52.

The distal end of the insert 56 is optionally rounded to avoid pressure points on the sutures. In some embodiments, the majority of the surface of the distal end 56 is planar with a curved outer boundary 57 along the edges.

In some embodiments, the insert body 52 has a length between the proximal end 54 and the distal end 56 within a range of about 4 mm to about 10 mm.

In some embodiments, the insert body 52 has a curved or circular cross-section as shown in FIG. 7B. In some embodiments, the insert body 52 has a cross-section that has at least one edge (i.e., is not entirely curved). For example, in some embodiments, such as when screwing is not required for insertion, the insert body 52 may have a triangular, quadrilateral (e.g., square or rectangular), pentagonal, hexagonal, octagonal, nonagonal, decagonal, asymmetrical, or any other cross-section desired by one of ordinary skill in the art.

In some embodiments, the insert body 52 has an outer diameter within a range of about 1.8 mm to about 4 mm. For example, the insert body 52 may have an outer diameter within a range of about 2 mm to about 3 mm.

In some embodiments, the insert 50 comprises a radiolucent material, such as polyetheretherketone (PEEK). In some embodiments, the insert 50 comprises a biocomposite or bioabsorbable material, such as polylactic acid (PLLA). In some embodiments, the insert 50 comprises a biodegradable material, such as polyglycolic acid (PGA). In some embodiments, the insert 50 comprises a combination of materials. In some embodiments, the insert 50 comprises the same material as the anchor body 20. In some embodiments, the insert 50 and the anchor body 20 comprise different materials.

Figures 8A, 8B, 8C, 8D, 8E:
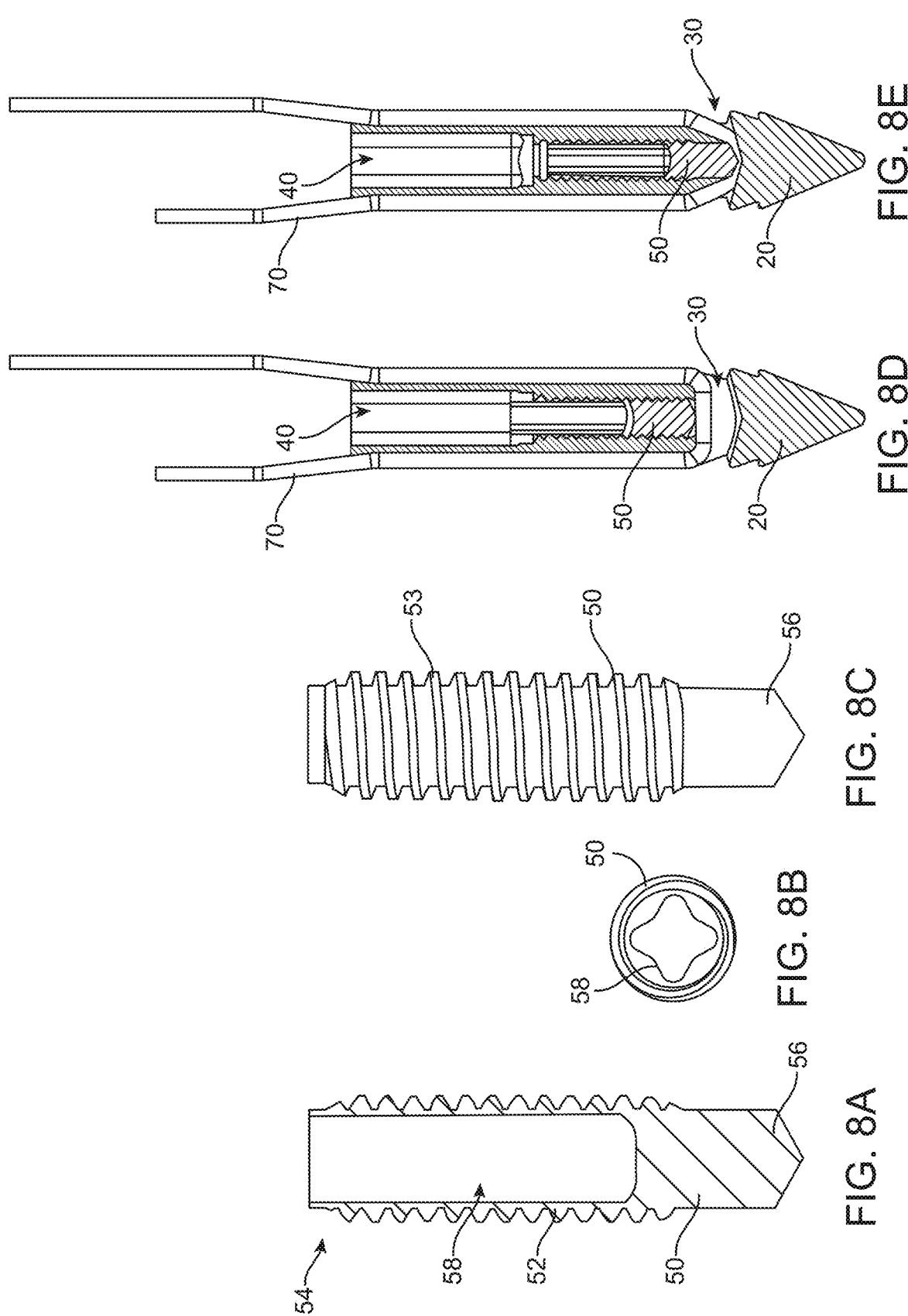
FIGS. 8A-8C show various views of an insert, in accordance with some embodiments.
FIGS. 8D and 8E show the insert of FIGS. 8A-8C in unlocked and locked configurations, respectively, within an anchor body in accordance with some embodiments.

FIGS. 8A-8C show various views of an insert 50. FIG. 8A shows a cross-sectional front view, FIG. 8B shows a top view, and FIG. 8C shows a front view. FIGS. 8D and 8E show the insert 50 of FIGS. 8A-8C in unlocked and locked configurations, respectively, within an anchor body 20 having a suture 70 threaded through a suture passage 30 as described herein. The anchor body 20 may be substantially similar to any of the anchor bodies described herein. The insert 50 may be substantially similar to any of the inserts described herein except that the distal end 56 is v-shaped to correspond to the v-shape of the distal surface 34 of the suture passage 30 of the anchor 10.

In some embodiments, the distal end 56 of the insert 50 is shaped to correspond to the distal surface 34 of the suture passage 30 of the anchor 10. For example, a bullet-shaped distal end 56 may correspond to a u-shaped distal surface 34 or a flat distal end 56 may correspond to a flat distal surface 34. Matching the shape of the distal end 56 of the insert 50 to the distal surface 34 of the suture passage 30 may help to distribute the pressure applied to the suture 70 by the insert 50 while still maintaining sufficient compression of the suture 70 to lock it in place when the insert 50 is in the locked configuration.

Figures 9A, 9B, 9C, 9D, 9E:
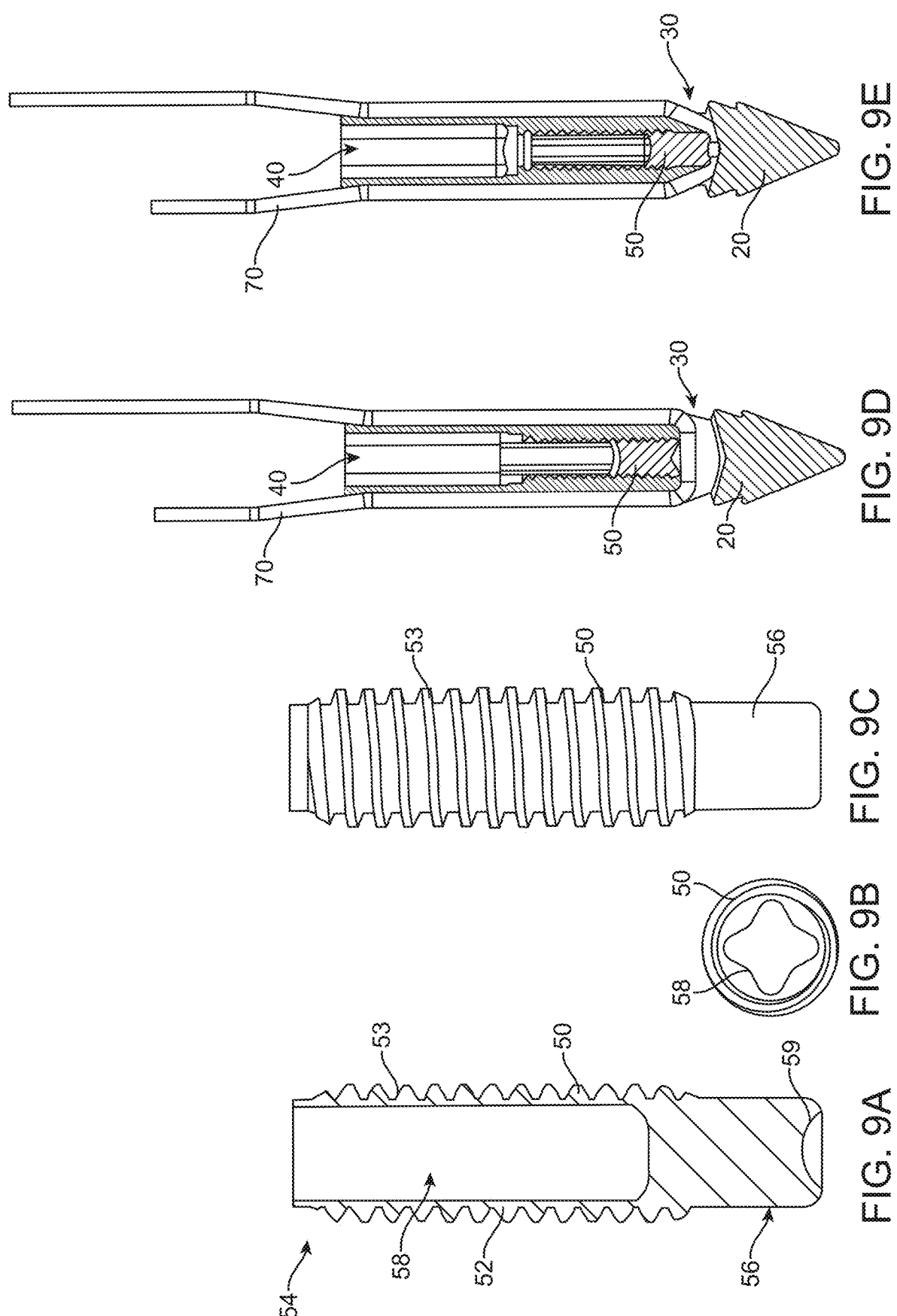
FIGS. 9A-9C show various views of an insert, in accordance with some embodiments.
FIGS. 9D and 9E show the insert of FIGS. 9A-9C in unlocked and locked configurations, respectively, within an anchor body in accordance with some embodiments.

FIGS. 9A-9C show various views of an insert 50. FIG. 9A shows a cross-sectional front view, FIG. 9B shows a top view, and FIG. 9C shows a front view. FIGS. 9D and 9E show the insert 50 of FIGS. 9A-9C in unlocked and locked configurations, respectively, within an anchor body 20 having a suture 70 threaded through a suture passage 30 as described herein. The anchor body 20 may be substantially similar to any of the anchor bodies described herein. The insert 50 may be substantially similar to any of the inserts described herein except that the distal end 56 has a dimpled surface 59. The dimpled surface 59 pinches the suture 70 against the distal surface 34 of the suture passage 30 at the outer edge of the insert 50 as opposed to the more central pinching of a rounded insert (e.g., as shown in FIG. 7A). In at least some instances, the dimple 59 reduces the surface area of the distal end 56 of the insert 50 touching the suture 70 which may make the suture 70 less likely to slide when then the insert 50 is being rotated into the locked configuration.

It will be understood by one of ordinary skill in the art that any of the inserts 50 described herein may be used in conjunction with any of the anchor bodies 20 described herein in order to achieve a desired distribution of pressure along the suture(s), a desired number and/or location of contact points with the suture(s), a desired amount of compression of the suture(s), or the like.

Figure 11:
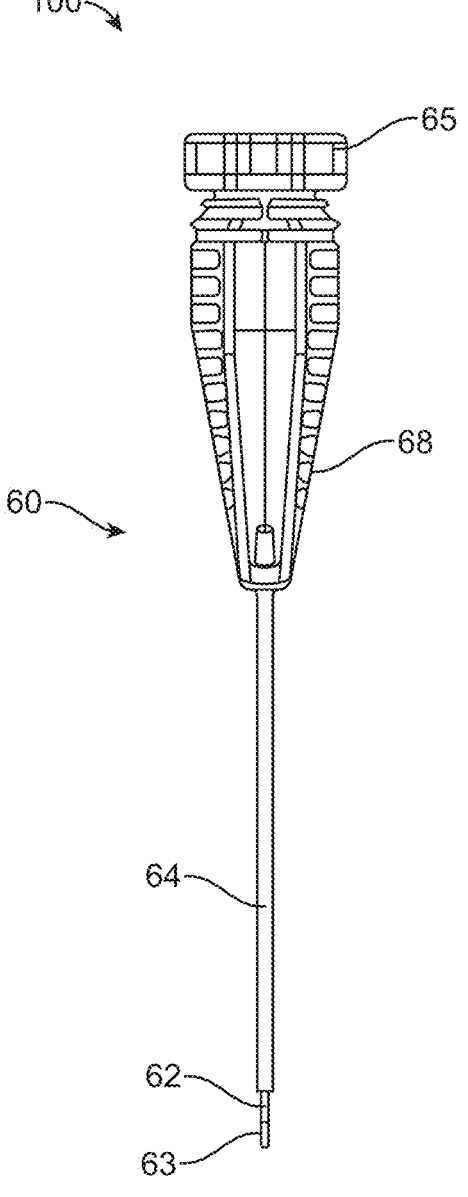
FIG. 11 shows a front view of a delivery device, in accordance with some embodiments.
Figure 12:
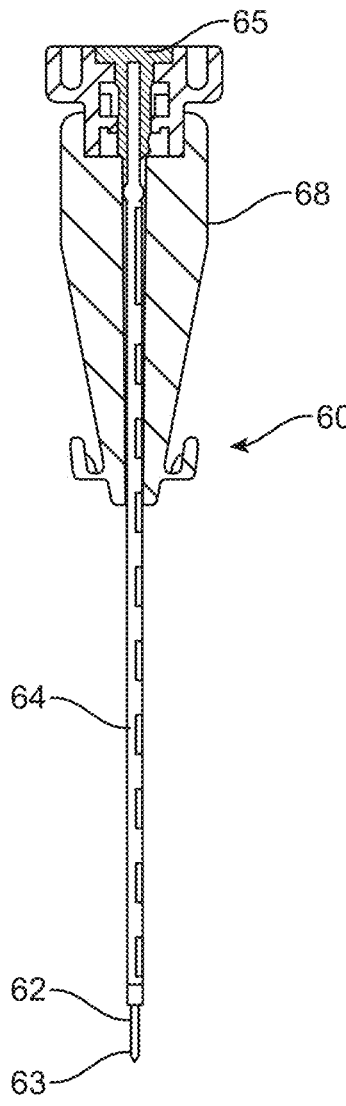
FIG. 12 shows a cross-sectional front view of the delivery device of FIG. 11, in accordance with some embodiments.
Figure 18C:
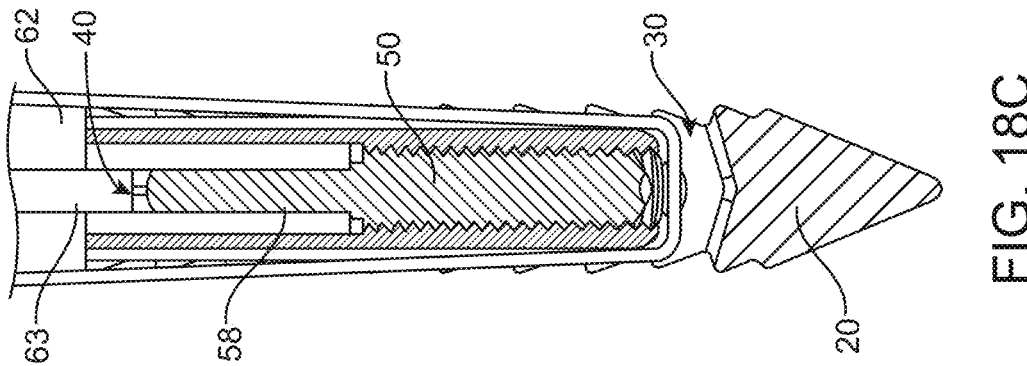
FIGS. 18B and 18C show front cross-sectional views of an anchor system comprising the insert of FIG. 18A, in accordance with some embodiments.

FIG. 10 shows a perspective view of a system 100 comprising a delivery device 60, an anchor 10, and an insert 50. FIG. 11 shows a front view of a delivery device 60. FIG. 12 shows a cross-sectional front view of the delivery device 60. The anchor 10 may be substantially similar to any of the anchors described herein. The insert 50 may be substantially similar to any of the inserts described herein. The delivery device 60 comprises an outer shaft 64, an inner shaft 62, a driver 63, and a handle 68. The outer shaft 64 optional comprises rotational markings 67 as described herein. The inner shaft 62 is configured to engage a proximal end of the anchor body 20 (e.g., with a proximal portion of the channel 40 as shown in FIG. 18C) during anchor delivery. In some embodiments, the inner shaft 62 may be inserted into a proximal portion of the channel and may engage with an inner surface of the channel. In some embodiments, the inner shaft 62 is longitudinally translatable relative to the outer shaft 64 so as to facilitate delivery and release of the anchor 10 therefrom. In some embodiments, the inner shaft 62 and the driver 63 are translatably disposed within the outer shaft 64. The driver 63 is configured to couple to a device coupler (e.g., device coupler 58 shown in FIG. 7D) of the insert 50 and facilitate longitudinal translation of the insert 50 within the channel of the anchor 10. The delivery device 60 optionally comprises a rotating knob 65 disposed on the handle 68. The knob 65 may be operably coupled to the driver 63 and configured to transmit rotational motion to the driver 63 (and from there to the insert 50). Rotation of the knob 65 may rotate the insert 50 along its threading and longitudinally translate the insert 50 within the anchor 10 as described herein. In some embodiments, the knob 65 can be replaced with a strike plate to enable impaction of the implant instead of rotation thereof depending on the method of translation desired.

In some embodiments, the delivery device 60 positions the anchor 10 within a pre-formed hole in a bone. The delivery device then rotates, axially impacts, or otherwise longitudinally translates the insert 50 relative to the anchor 10 to lock a suture within the anchor body 20. In some embodiments, the pre-formed hole is generated using a drill. In some embodiments, the pre-formed hole is generated using an awl.

In some embodiments, the inner shaft 62, outer shaft 64, and/or driver 63 comprise stainless steel. In some embodiments, the inner shaft 62, outer shaft 64, and/or driver 63 comprise hardened steel alloy.

In some embodiments, the inner shaft 62, outer shaft 64, and/or driver 63 are cannulated.

In some embodiments, the inner shaft 62, outer shaft 64, and/or driver 63 are knurled at the opposite end from anchor device 10 to facilitate handle attachment.

In some embodiments, the outer shaft 64 has an outer diameter sufficient to fit into a cannulated guide tube.

In some embodiments, the handle 68 comprises plastic. In some embodiments, the handle 68 is overmolded. In some embodiments, the handle 68 comprises Makrolon. In some embodiments, the handle 68 comprises ABS. In some embodiments, the handle 68 comprises glass-filled ABS. In some embodiments, the handle 68 is coupled to the outer shaft 64 with a medical-grade adhesive. In some embodiments, the handle 68 is coupled to the outer shaft 64 with a press-fit.

In some embodiments, the delivery device 60 has depth markings. The depth markings may help surgeons to determine how far the delivery device 60 has been placed within a patient. In some embodiments, delivery device 60 may have laser marking(s) showing suture orientation (e.g., rotational markings 67 shown in FIG. 1) and proper insertion depth.

In some embodiments, the anchor 10 may be placed within a patient using a device or devices other than delivery device 60. Examples of additional insertion devices that may be used to implant the anchor 10 into a patient include manual insertion with standard surgical instruments. In some examples, an insertion device may include a lighting and/or camera component so as to help guide a surgeon when placing the anchor within a patient.

Figure 13:
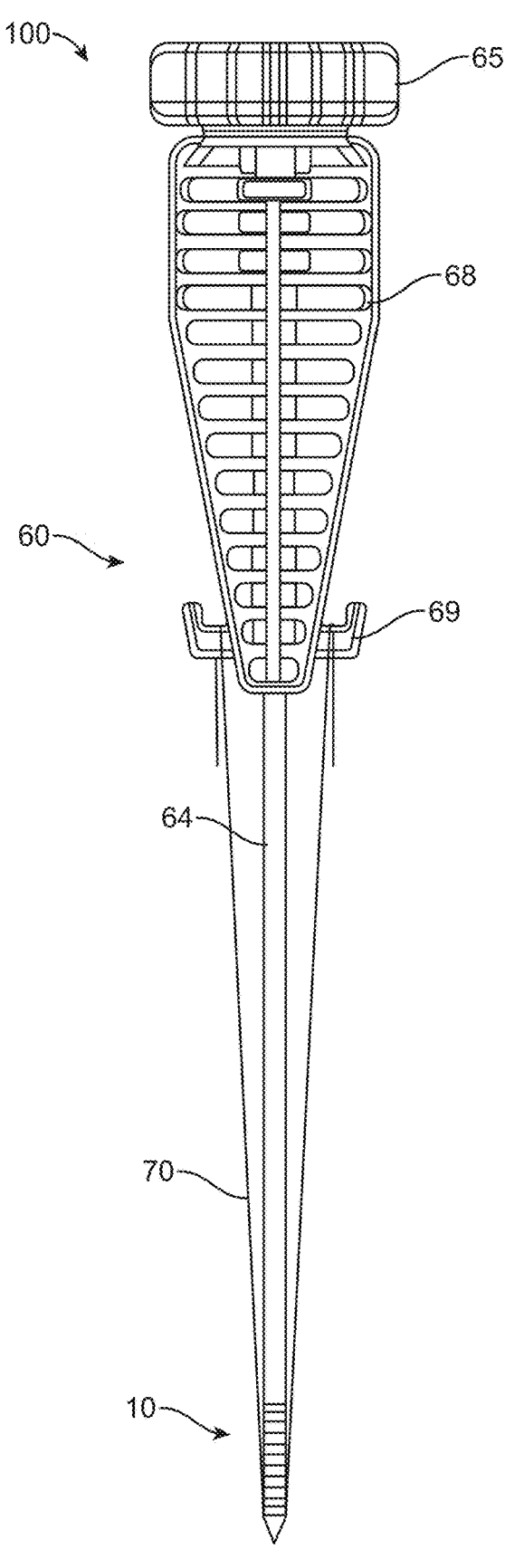
FIG. 13 shows a front view of the system of FIG. 10 including a suture disposed within the suture passage, in accordance with some embodiments.
Figure 14:
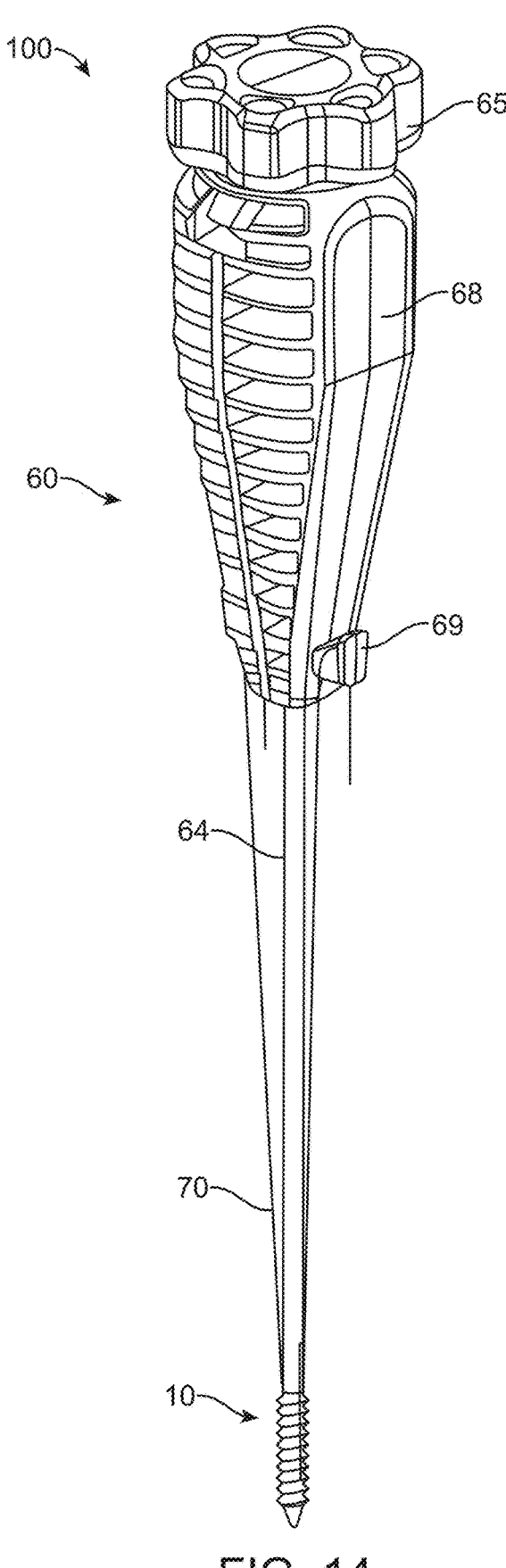
FIG. 14 shows a perspective view of the system of FIG. 13, in accordance with some embodiments.

FIG. 13 shows a front view of the system 100 of FIG. 10 including a suture 70 disposed within the suture passage 30 of the anchor 10. FIG. 14 shows a perspective view of the system 100 with suture 70. The suture 70 is wrapped around cleats 69 on handle 68 of the delivery device 60. In some instances, the surgeon may utilize the cleats to hold tension on the suture 70 and/or anchor 10 during the implantation procedure. Alternatively, or in combination, the suture 70 is wrapped around the cleats 69 in order to hold the anchor 10 in position against the distal end of the delivery device 60 prior to implantation (e.g., during shipping or preparation of the surgical site).

Figures 15A, 15B, 15C:
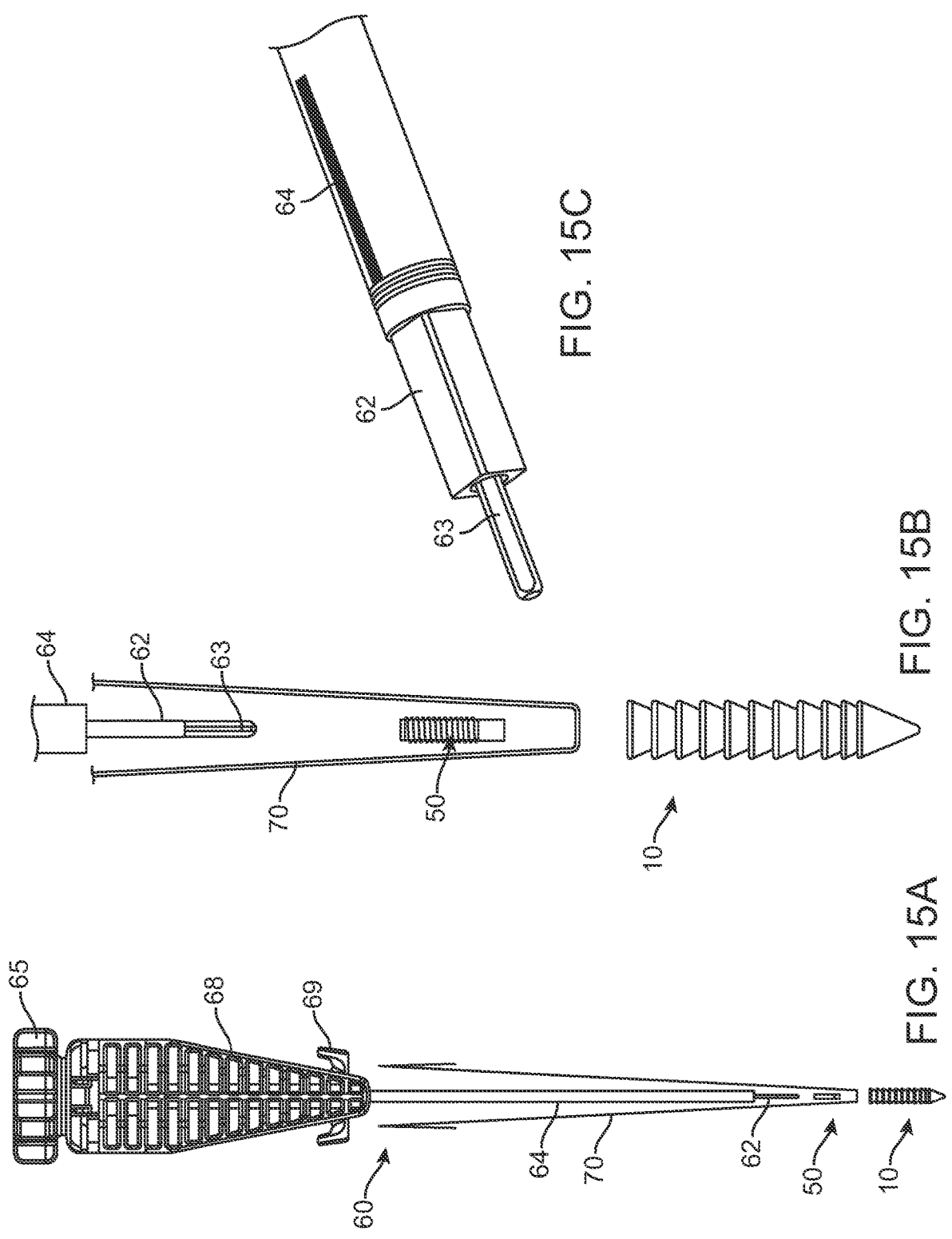
FIG. 15A shows an exploded view of the system of FIG. 13, in accordance with some embodiments.
FIG. 15B shows an exploded view of the distal end of the delivery device, the insert, and the anchor of the system of FIG. 15A, in accordance with some embodiments.
FIG. 15C shows a perspective view of the distal end of the delivery device of FIG. 15A, in accordance with some embodiments.

FIG. 15A shows an exploded view of the system 100 of FIG. 13. FIG. 15B shows an exploded view of the distal end of the delivery device 60, the insert 50, and the anchor 10 of the system 100. FIG. 15C shows a perspective view of the distal end of the delivery device 60. The delivery device 60 comprises an outer shaft 64, an inner shaft 62, and a driver 63. In some embodiments, the inner shaft 62 and the driver 63 are translatably disposed within the outer shaft 64. The driver 63 is configured to couple to a correspondingly-shaped device coupler (e.g., device coupler 58 shown in FIG. 7D) of the insert 50 and facilitate longitudinal translation of the insert 50 within the channel of the anchor 10. In some embodiments, the driver 63 is a male driver 63 having a shape corresponding to a cavity (e.g., as shown in FIG. 7D) in the insert 50. In some embodiments, the driver 63 is a female driver 63 having a shape corresponding to a proximal protrusion (e.g., as shown in FIG. 18A) of the insert 50. The driver 63 may be operably coupled to the insert 50 and configured to transmit rotational motion to the insert 50. In some embodiments, rotation of the driver 63 relative to the inner shaft 62 and/or outer shaft 64 may rotate the insert 50 along its threading and longitudinally translate the insert 50 within the anchor 10 as described herein. In some embodiments, the driver 63 may be operably coupled to the insert 50 and configured to impact the insert 50 in addition to or instead of rotating the insert 50.

Figures 16A, 16B, 16C, 16D:
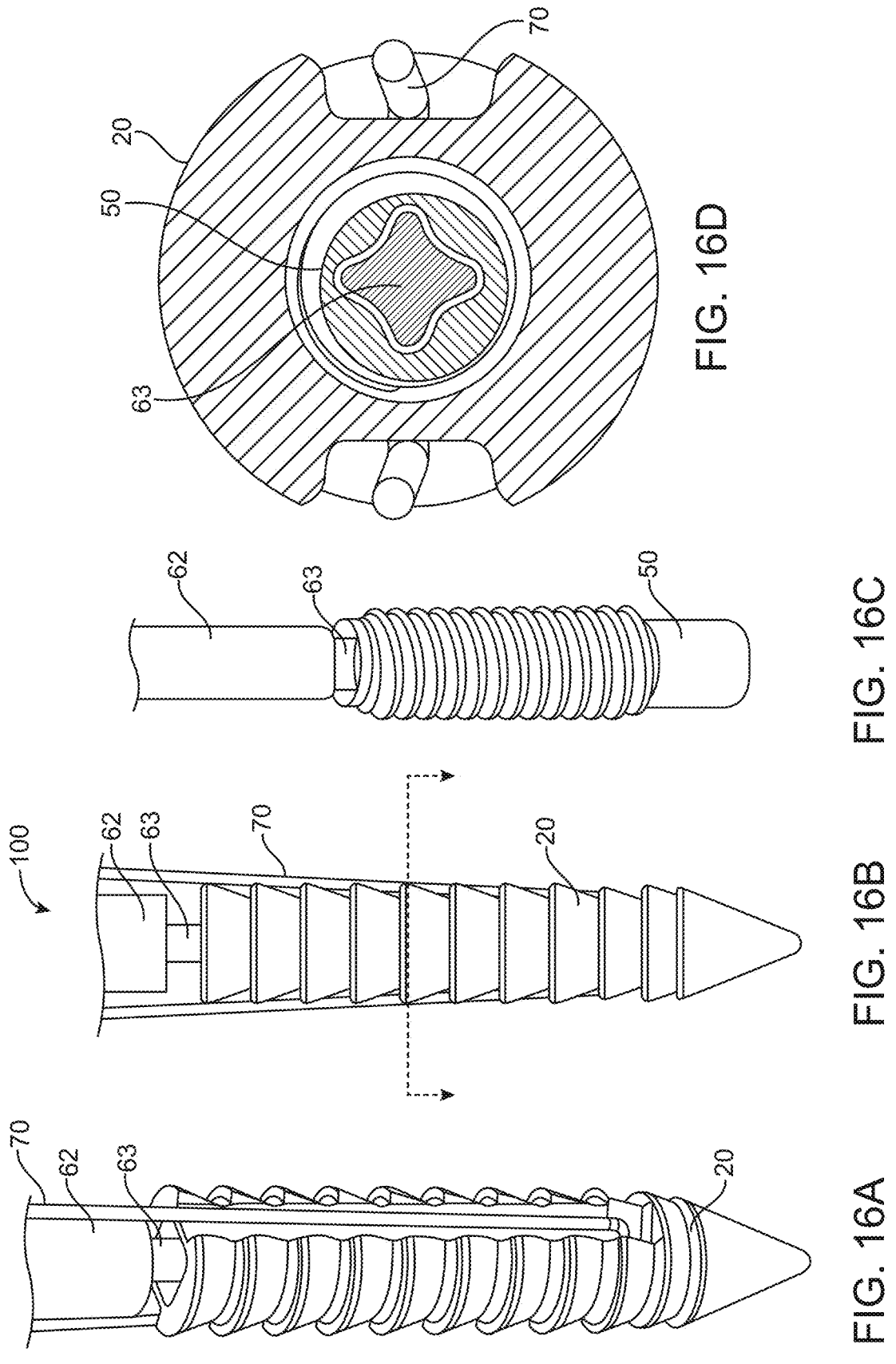
FIGS. 16A-16D show various views of the interaction of the distal end of a delivery device with an anchor and insert, in accordance with some embodiments.

FIGS. 16A-16D show various views of the interaction of the distal end of a delivery device 60 with an anchor 10 and insert 50. The delivery device 60 comprises an inner shaft 62 and a driver 63 as described herein. FIG. 16A shows a perspective view of the distal end of the delivery device 60 coupled to the anchor body 20. FIG. 16B shows a front view of the anchor body 20 of FIG. 16A. FIG. 16C shows a perspective view of the distal end of the delivery device 60 coupled to the insert 50. FIG. 16D shows a top cross-sectional view of the system 100 of FIG. 16B. The inner shaft 62 and the insert 50 are rotationally coupled to one another. Rotation of the driver 63 relative to the inner shaft 62 rotates the insert 50 within the channel 40 relative to the anchor body 20 in order to translate the insert 50 therewithin along the threads of the channel and the insert 50 as described herein.

FIGS. 17A and 17B show front cross-sectional views of an anchor system 100 in unlocked and locked configurations, respectively. The system 100 comprises an anchor 10 and an insert 50 disposed within a channel 40 of the anchor body 20. The anchor 10 may be substantially similar to any of the anchors described herein except that the inner surface of the channel does not comprise threading. The insert 50 may be substantially similar to any of the inserts described herein. The outer surface of the insert 50 may not comprise threading. The channel 40 and insert 50 are configured to longitudinally translate without requiring relative rotation therebetween. In some embodiments, the insert 50 is configured to be press-fit into the channel 40.

FIG. 18A shows a front cross-sectional view of an exemplary insert 50 having a male device coupler 58. The insert 50 may be substantially similar to any of the inserts described herein except that the coupler 58 comprises a proximal protrusion extending proximally from the proximal end of the insert body 52.

Figure 18B:
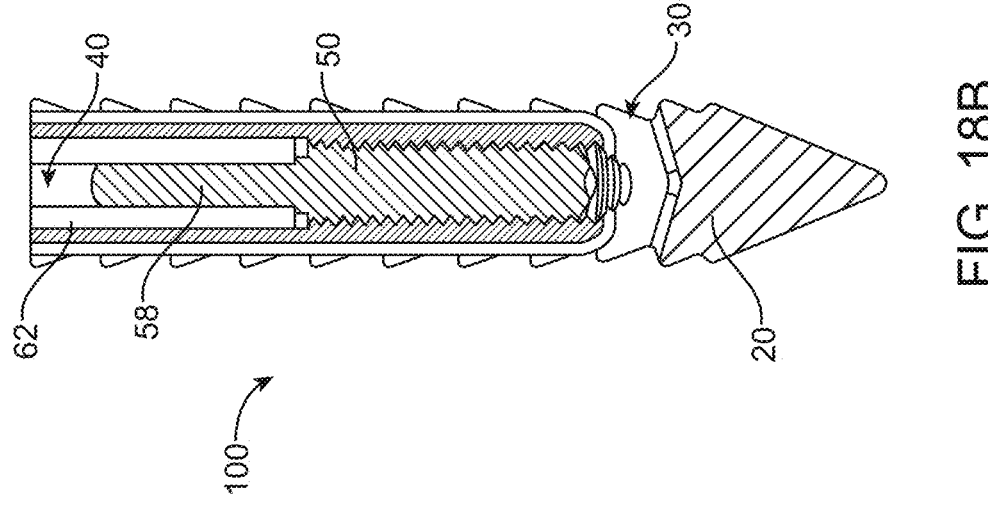
Figure 18A:
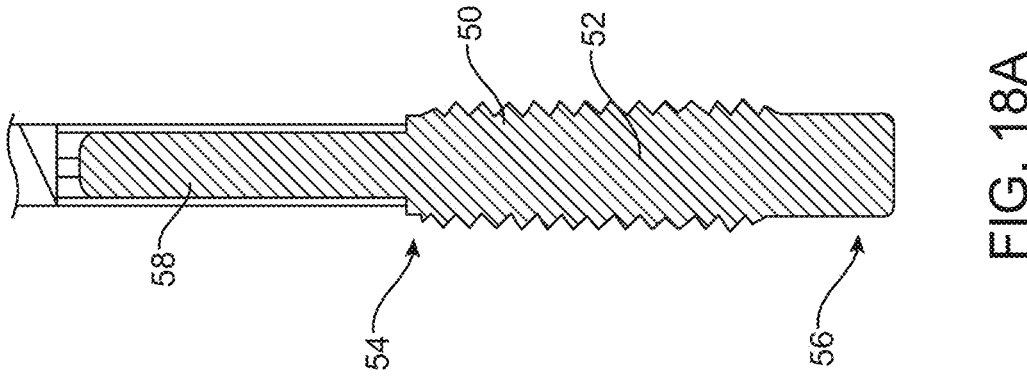
FIG. 18A shows a front cross-sectional view of an exemplary insert having a male device coupler, in accordance with some embodiments.

FIGS. 18B and 18C show front cross-sectional views of an anchor system 100 comprising the insert 50 of FIG. 18A. FIG. 18B shows the insert 50 in the channel 40 of the anchor body 20 in an unlocked configuration. FIG. 18C shows the system of FIG. 18B coupled to a suture 70 and delivery device driver 63. The delivery device driver 63 is configured to rotate and/or longitudinally translate the insert 50 within the channel 40 as described herein.

Figures 19A, 19B, 19C, 19D:
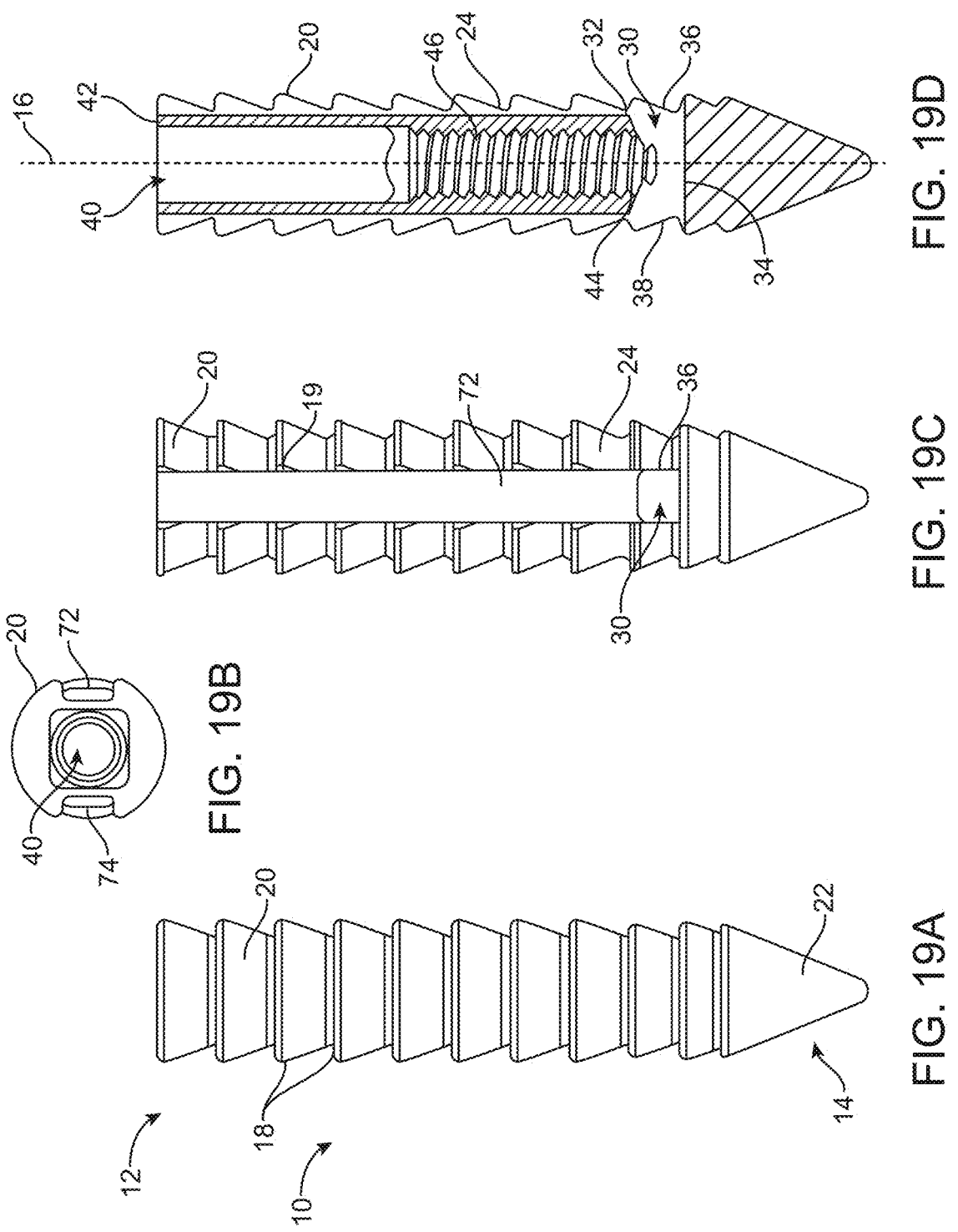
FIGS. 19A-19D show various views of an anchor body comprising a suture passage with a substantially flat distal surface, in accordance with some embodiments.

FIGS. 19A-19D show various views of an anchor 10 comprising a suture passage 30 with a substantially flat distal surface 34, in accordance with some embodiments. FIG. 19A shows a front view, FIG. 19B shows a top view, FIG. 19C shows a front view rotated 90° relative to FIG. 19A, and FIG. 19D shows a front cross-sectional view. The anchor 10 may be substantially similar to any of the anchors described herein. The suture passage 30 comprises a proximal surface 32 and a distal surface 34.

The distal surface 34 of the suture passage 30 is optionally substantially flat. In some embodiments, the flat distal surface 34 is substantially perpendicular to the longitudinal axis 16 of the anchor body 20. The flat distal surface 34 provides a surface without sharp edges and therefore enables distribution of forces along a length of the suture 70 instead of concentrated pressure points (which occur with sharp edges) when the insert 50 is in the locked configuration. In at least some instances, spreading the forces over a length of the suture will benefit suture integrity, enabling better locking, less strain on the suture, and reduced risk to patients that the suture will fail after implantation.

Figures 20A, 20B, 21A, 21B:
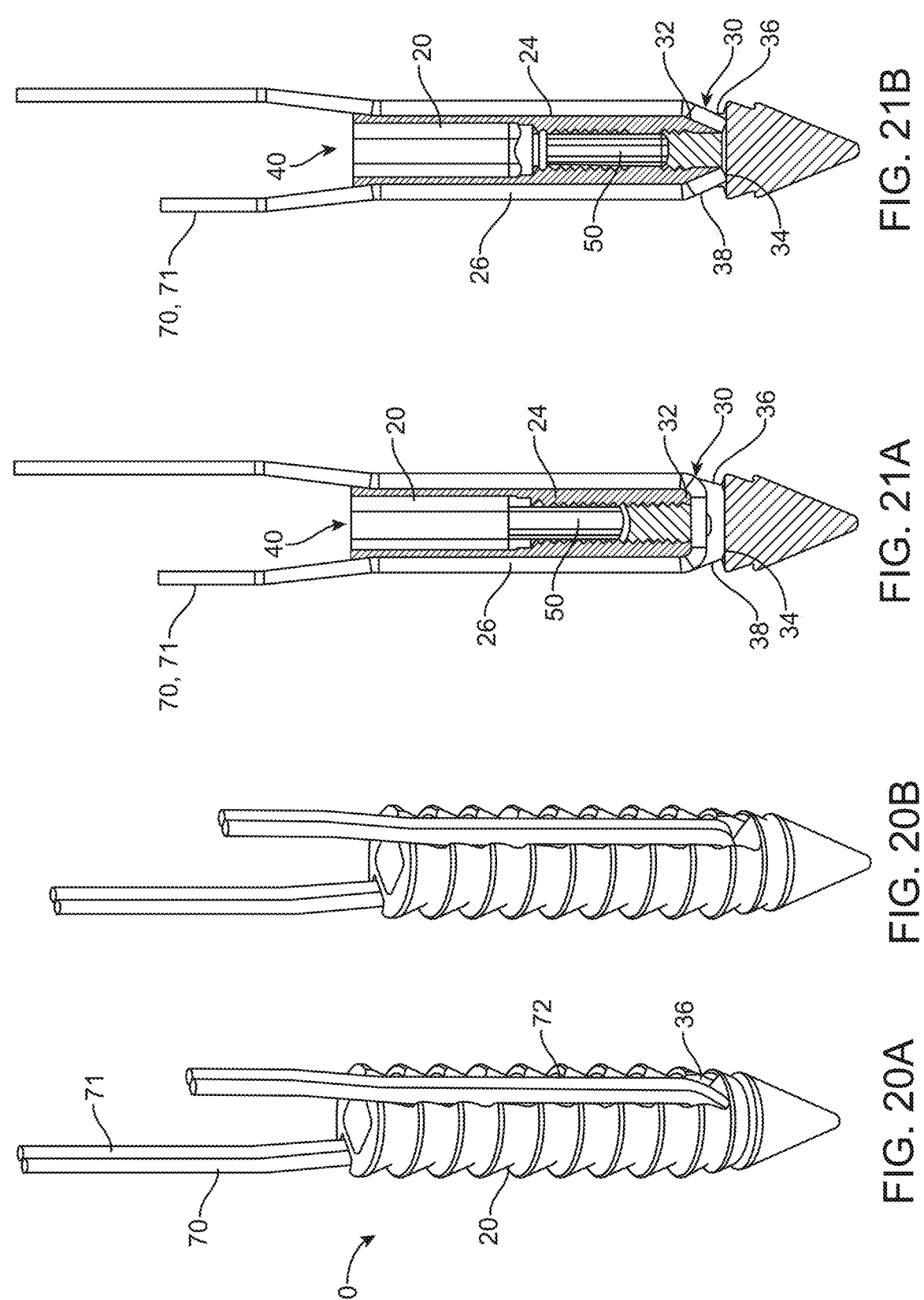
FIGS. 20A and 20B show isometric views of an anchor system comprising the anchor of FIGS. 19A-19D and two sutures in locked and unlocked configurations, respectively, in accordance with some embodiments.
FIGS. 21A and 21B show front cross-sectional views of the system of FIGS. 20A-20B in the unlocked and locked configurations, respectively, in accordance with some embodiments.

FIGS. 20A and 20B show isometric views of an anchor system comprising the anchor 10 of FIGS. 19A-19D and two sutures 70, 71 in locked and unlocked configurations, respectively.

FIGS. 21A and 21B show front cross-sectional views of the system of FIGS. 20A-20B in the unlocked and locked configurations, respectively. FIG. 21A shows the insert 50 in an unlocked configuration. FIG. 21B shows the insert 50 in a locked configuration. The insert 50 is disposed within a channel 40 extending along the longitudinal axis 16 of the anchor body 20 from a proximal opening 42 to a distal opening 44 in the proximal surface 32 of the suture passage 30. Longitudinal translation of the insert 50 within the channel 40 towards the distal surface 34 of the suture passage 30 from the unlocked configuration to the locked configuration compresses the suture 70 between the distal end 56 of the insert 50 and the distal surface 34 of the suture passage 30 in order to secure the suture 70 in the suture passage 30 as described herein.

Figures 22A, 22B, 22C:
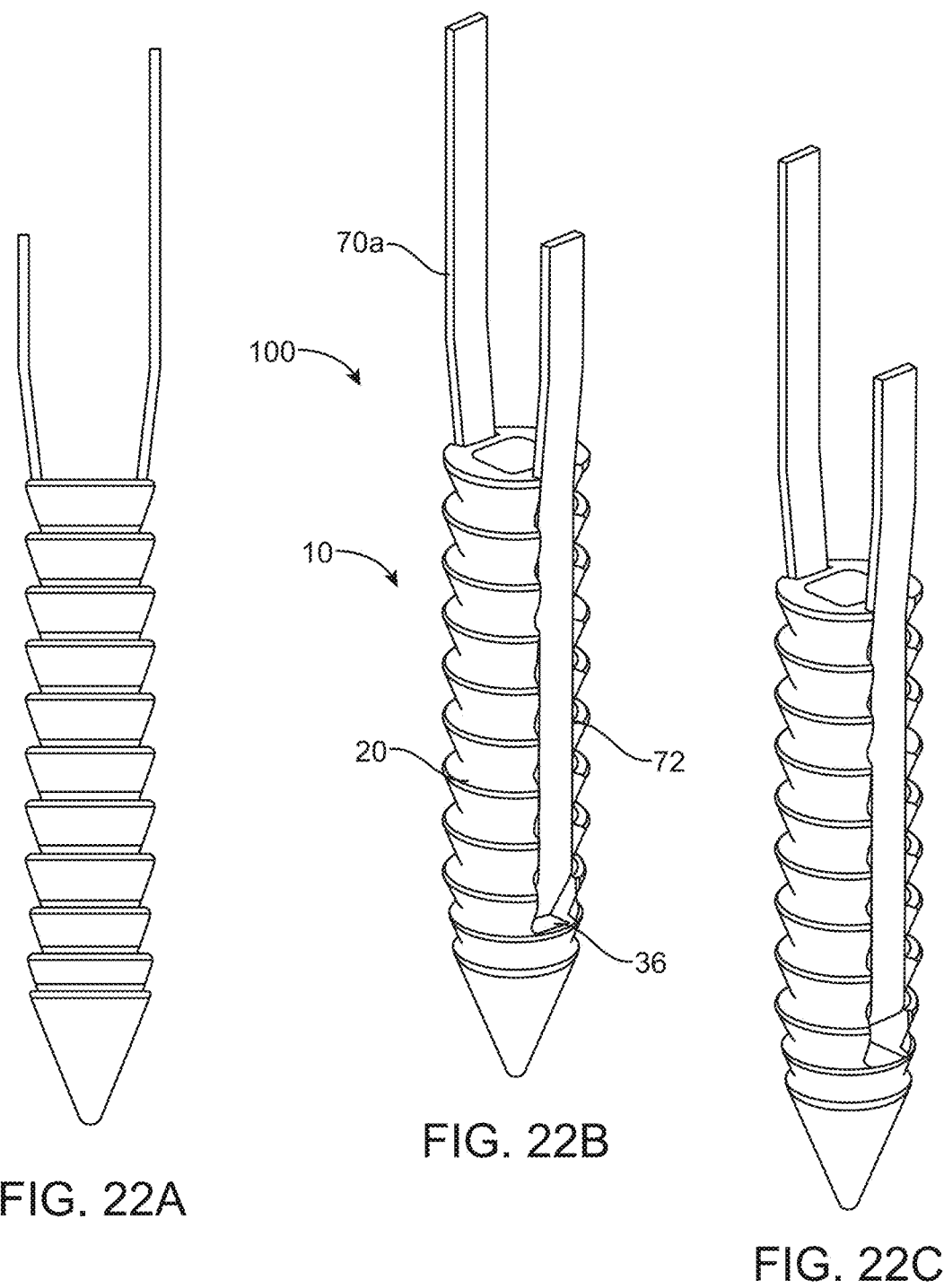
FIGS. 22A-22C show various views of an anchor system comprising the anchor of FIGS. 19A-19D and a suture tape, in accordance with some embodiments.

FIGS. 22A-22C show various views of an anchor system 100 comprising the anchor 10 of FIGS. 19A-19D and a suture tape 70a. FIG. 22A shows a front view, FIG. 22B shows an isometric view in the locked configuration, and FIG. 22C shows an isometric view in the unlocked configuration. The suture groove 72 (and other suture grooves described herein, e.g., suture groove 74) may be recessed relative to the one or more external retention features 18 to ensure that a suture tape 70a disposed therealong does not protrude outward past the external retention feature(s) 18 to contact the bone, when the anchor is inserted within the bone. Compared to a rounded or square suture, suture tape 70a has a thinner and wider profile, the shape of the groove 72 (and other grooves) and suture passage 30 may be adjusted to accommodate the different shape and size of the suture tape 70a so the suture tape 70a lies flat therein. For example, the suture groove 72 may have a width within a range of about 1 mm to about 3 mm, for example within a range of about 1.8 mm to about 2 mm. The suture passage 30 can be dimensioned to compress one or more suture tapes 70a therein with the insert 50. The suture tape 70a can have a rounded tail in order to facilitate its uses with the same instruments and procedures as traditional sutures.

FIGS. 23A and 23B show front cross-sectional views of the system 100 of FIGS. 22A-22C in the unlocked and locked configurations, respectively. FIG. 23A shows the insert 50 in an unlocked configuration. FIG. 23B shows the insert 50 in a locked configuration. The insert 50 is disposed within a channel 40 as described herein. Longitudinal translation of the insert 50 within the channel 40 towards the distal surface 34 of the suture passage 30 from the unlocked configuration to the locked configuration compresses the suture tape 70a between the distal end 56 of the insert 50 and the distal surface 34 of the suture passage 30 in order to secure the suture 70 in the suture passage 30 as described herein.

Figures 24A, 24B, 24C, 25A, 25B:
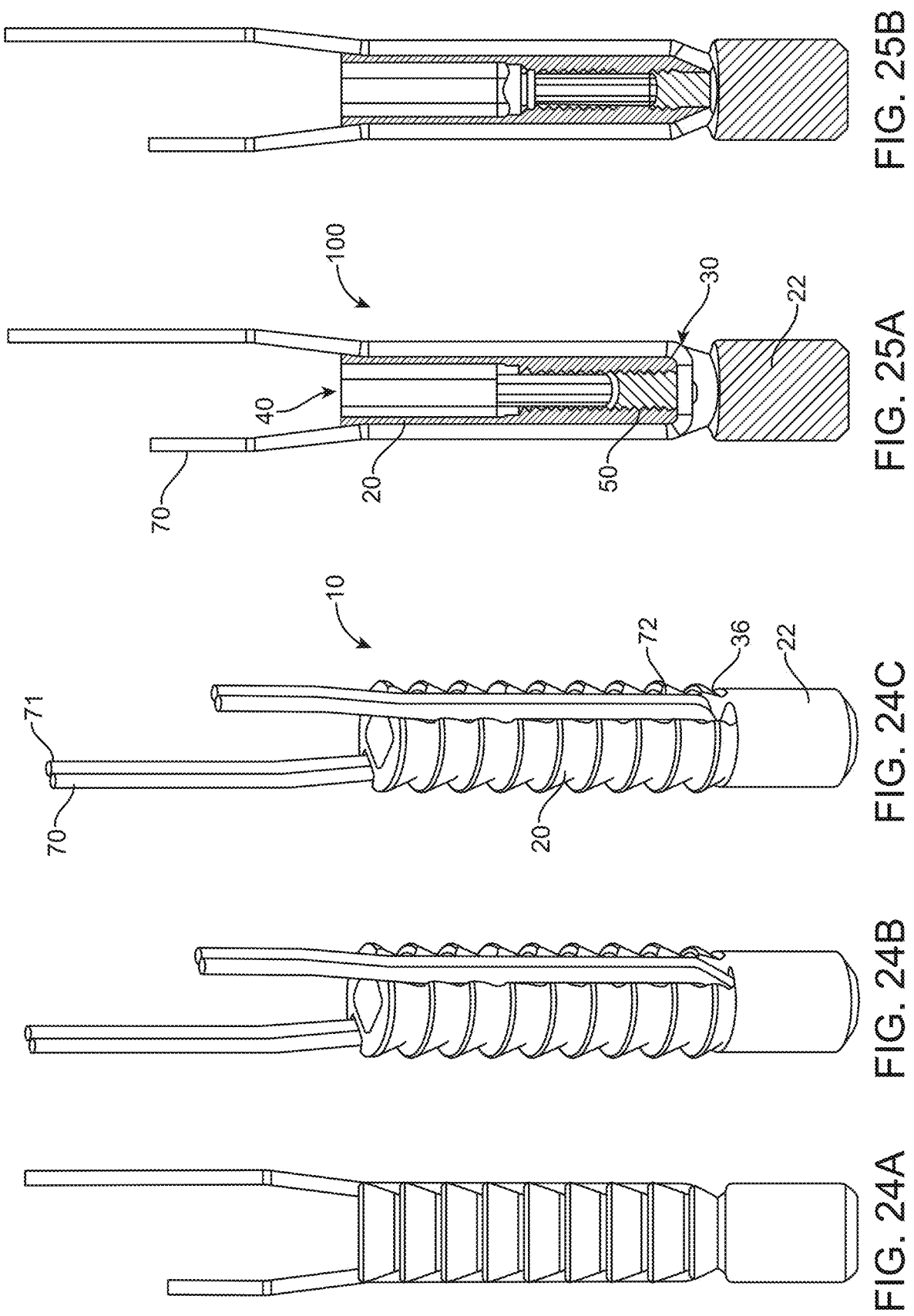
FIGS. 24A-24C show various views of an anchor system comprising an anchor with a blunt distal tip, in accordance with some embodiments.
FIGS. 25A and 25B show front cross-sectional views of the system of FIGS. 24A-24C in the unlocked and locked configurations, respectively, in accordance with some embodiments

FIGS. 24A-24C show various views of an anchor system 100 comprising an anchor 10 with a blunt distal tip 22. FIG. 24A shows a front view, FIG. 24B shows an isometric view in the locked configuration, and FIG. 24C shows an isometric view in the unlocked configuration. The anchor 10 may be substantially similar to any of the anchors described herein except that the distal tip 22 is blunt.

FIGS. 25A and 25B show front cross-sectional views of the system 100 of FIGS. 24A-24C in the unlocked and locked configurations, respectively. FIG. 25A shows the insert 50 in an unlocked configuration. FIG. 25B shows the insert 50 in a locked configuration. The insert 50 is disposed within a channel 40 as described herein. Longitudinal translation of the insert 50 within the channel 40 towards the distal surface 34 of the suture passage 30 from the unlocked configuration to the locked configuration compresses the suture 70 between the distal end 56 of the insert 50 and the distal surface 34 of the suture passage 30 in order to secure the suture 70 in the suture passage 30 as described herein.

Figures 26A, 26B, 26C, 26D, 26E:
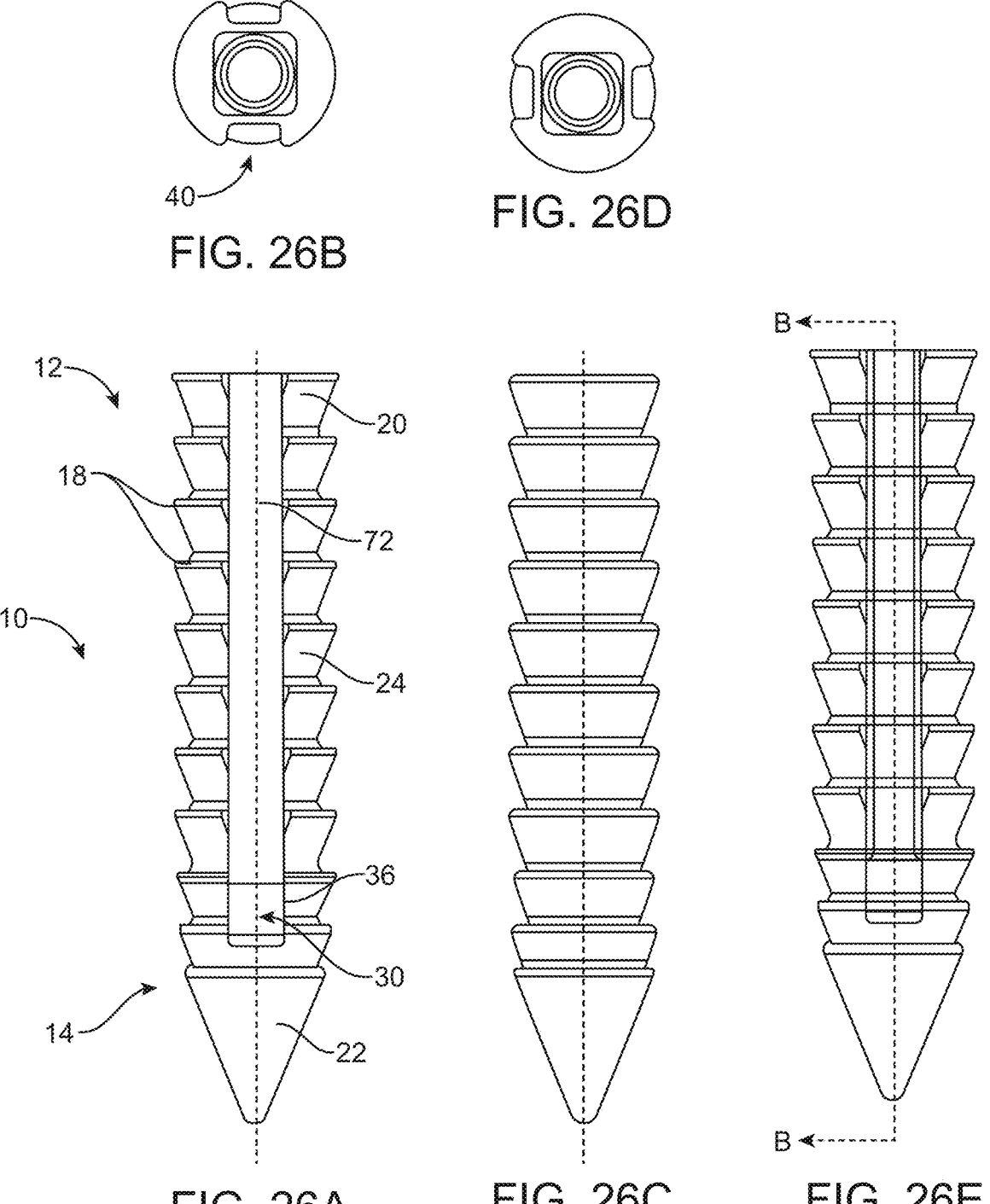
FIGS. 26A-26E show various views of an anchor body, in accordance with some embodiments.

FIGS. 26A-26E show various views of an anchor 10. FIG. 26A shows a front view, FIG. 26B shows a top view of FIG. 26A, FIG. 26C shows a front view rotated 90° relative to FIG. 26A, FIG. 26D shows a top view of FIG. 26C, and FIG. 26E shows a front view rotated 180° relative to FIG. 26A. The anchor 10 may be substantially similar to any of the anchors described herein.

Figures 27A, 27B:
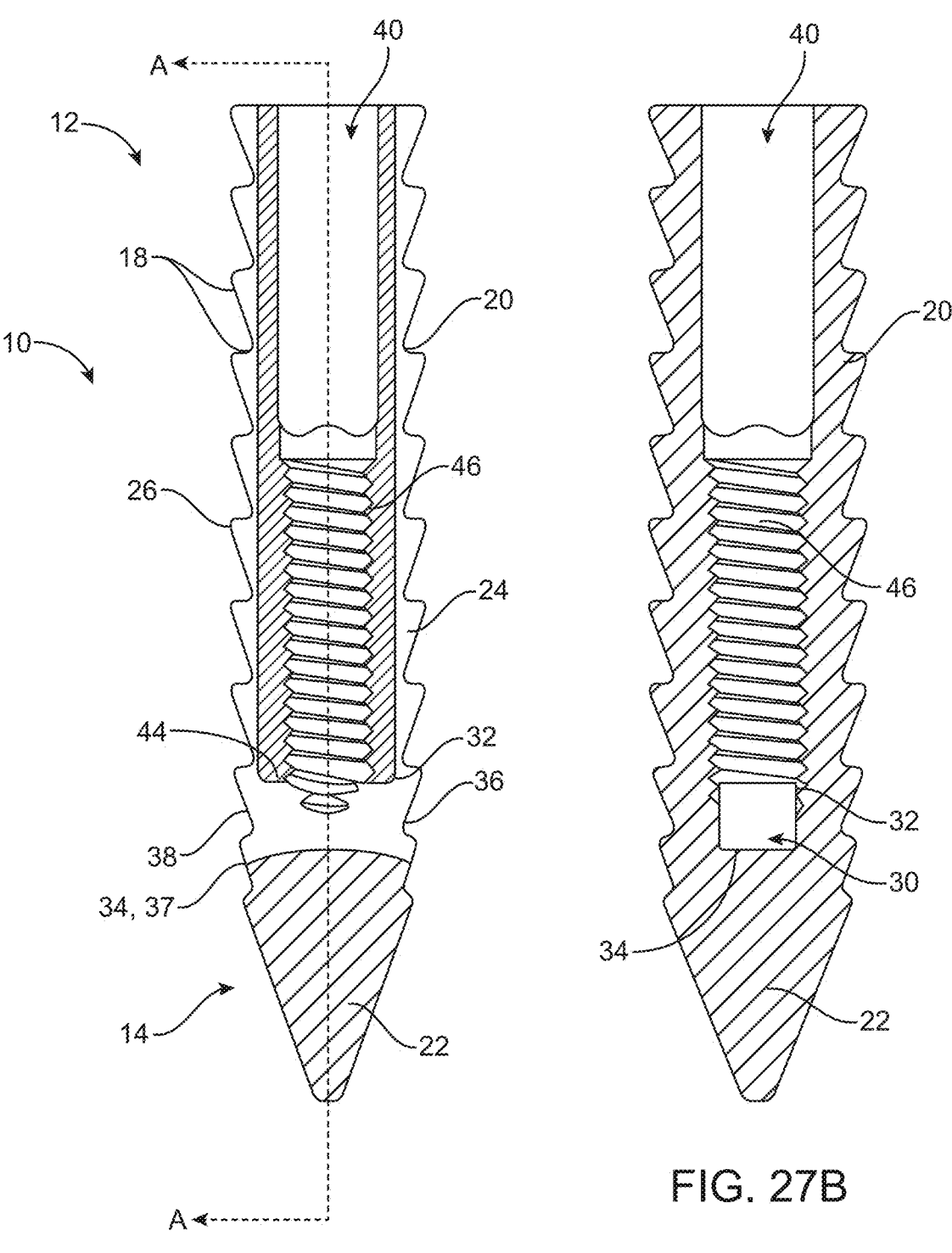
FIGS. 27A-27D show front cross-sectional view of the anchor of FIGS. 26A-26E, in accordance with some embodiments.
Figure 27D:
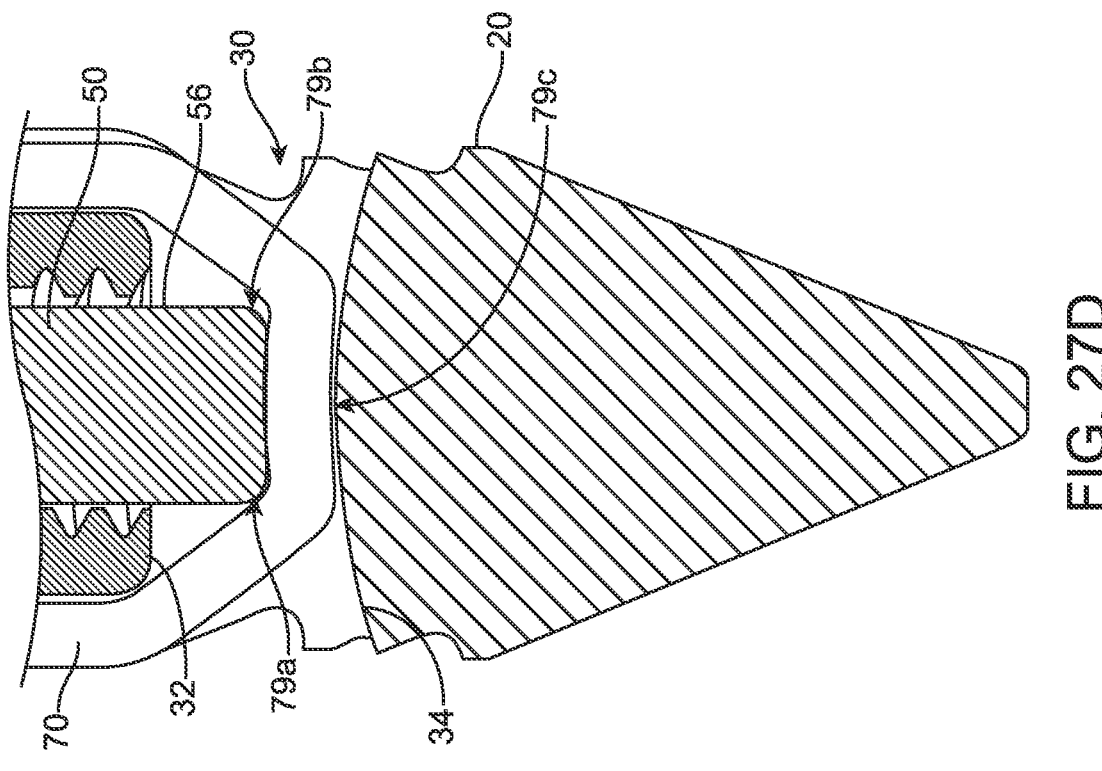
Figure 27C:
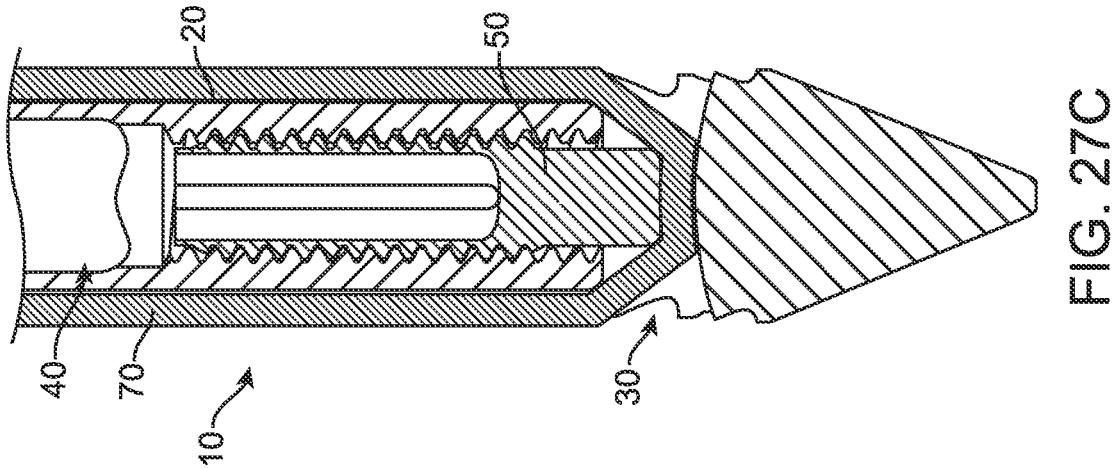

FIGS. 27A and 27B show front cross-sectional view of the anchor 10 of FIGS. 26A-26E. FIG. 27A shows a front-crosssectional view taken along line B-B of FIG. 26E. FIG. 27B shows a front-cross-sectional view taken along line A-A of FIG. 27A. FIG. 27C shows a front cross-sectional view of the anchor 10 with an insert 50 locking a suture 70 therein. FIG. 27D shows a front cross-sectional view of the suture passage 30 with locked suture 70 disposed therein. The suture passage 30 comprises a proximal surface 32 and a distal surface 34. The distal surface 34 of the suture passage 30 optionally comprises a convex curvature 37 extending proximally towards the distal opening 44 of the channel 40. In some embodiments, the convex curvature 37 extends into the distal opening 44 of the channel 40. In some embodiments, the convex curvature 37 spans the entire distal surface 34 of the suture passage 30.

The convex curvature 37 provides a surface without sharp edges and therefore enables distribution of forces along a length of the suture 70 instead of concentrated pressure points (which occur with sharp edges) when the insert 50 is in the locked configuration. In at least some instances, spreading the forces over a length of the suture will benefit suture integrity, enabling better locking, less strain on the suture, and reduced risk to patients that the suture will fail after implantation.

In some embodiments, three or more points of capture of the suture 70 exist within the suture passage 30. For example, when the distal surface 34 of the suture passage 30 is convex, the suture 70 is captured by at least a first capture point 79a, a second capture point 79b, and a third capture point 79c. The first capture point 79a may be between the suture 70 and a first lateral side of the distal end 56 of the insert 50. The second capture point 79b may be between the suture 70 and a second lateral side of the distal end 56 of the insert 50. The third capture point 79c may be between the distal end 56 of the insert 50 and the distal surface 34 of the suture passage 30. In at least some instances, providing three or more capture points will increase the pull-out force necessary to dislodge the suture 70 and provide better securing of the suture 70 after implantation.

The convex curvature 37 can have an arc angle within a range of about 3.5° to about 15°. For example, the convex curvature 37 can have an arc angle of about 5.75°.

Figures 28A, 28B, 28C, 28D:
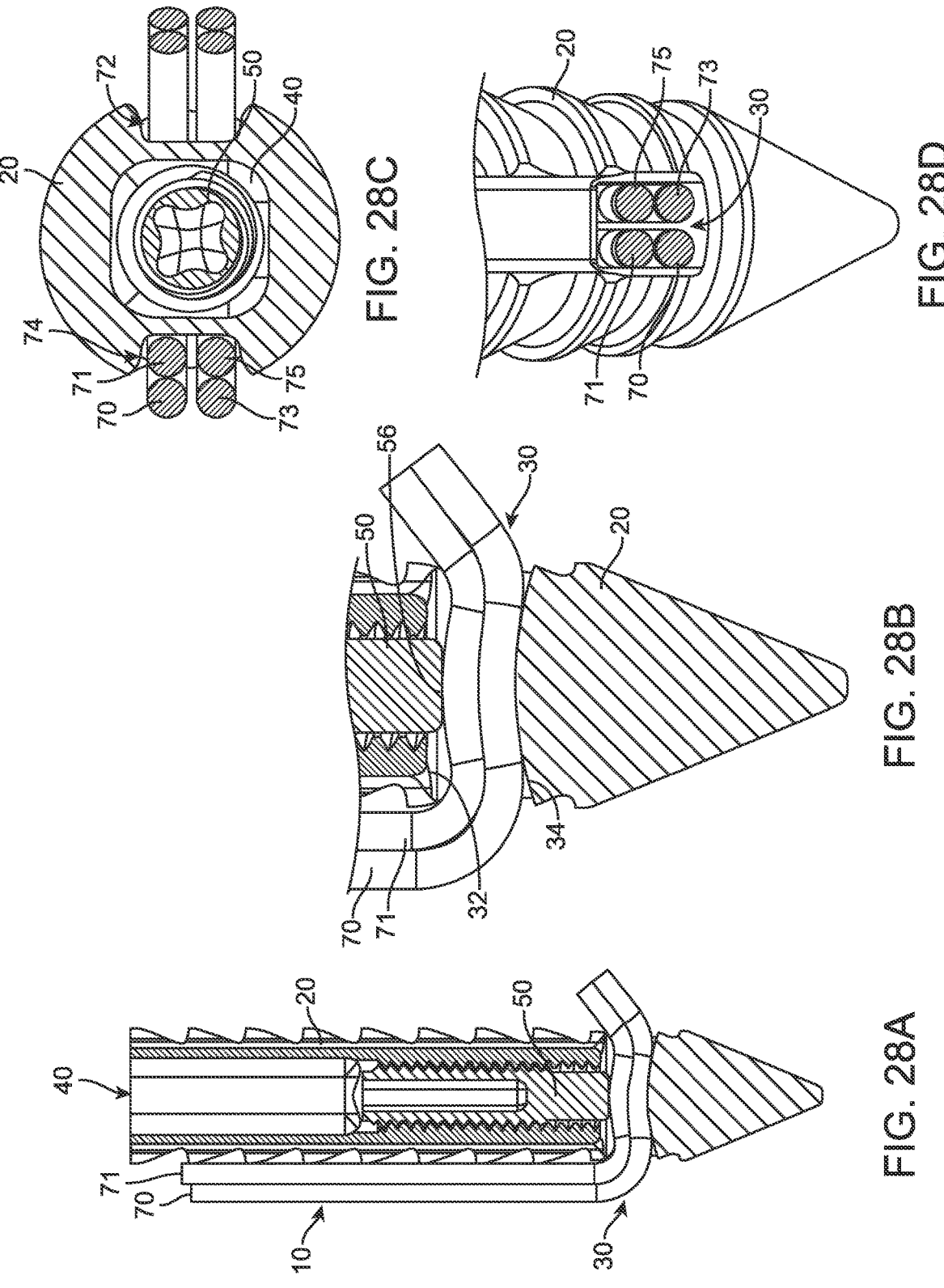
FIGS. 28A-28D show various views of four sutures locked within an anchor body, in accordance with some embodiments.

FIGS. 28A-28D show various views of four sutures 70, 71, 73, 75 locked within an anchor body 20. FIG. 28A shows a cross-sectional front view of the anchor body 20. FIG. 28B shows a cross-sectional front view of the suture passage 30. FIG. 28C shows a top view of the anchor body 20. FIG. 28D shows a perspective view of the suture passage 30 with convex distal surface 34. As will be understood by one of ordinary skill in the art based on the teachings herein, one or more sutures may be disposed within the suture passage 30 and suture grooves 72, 74 of the anchors 10 described herein. For example, one, two, three, or four sutures may be disposed within the suture passage 30. In at least some instances, the use of two or more sutures may add strength and/or reduce the risk of suture failure compared to a single suture alone. The number of sutures may be selected based on the surgical method (e.g., the size of a rotator tear can determine the number of anchors and sutures used whereas a bicep tendon repair typically only has two tails (one suture) which wrap around the tendon), physiology, and/or surgeon preference.

For example, four or more sutures may be disposed within the suture passage 30. The four sutures 70, 71, 73, 75 may be disposed within the suture passage 30 such that two sutures lie on top of the other two sutures. For example, the second suture 71 may be stacked above the first suture 70 and the fourth suture 75 may sit above the third suture 73.

The two pairs of sutures may sit side by side within the suture passage 30. The stacked suture pairs can be locked between the distal surface 34 of the suture passage 30 and the distal end 56 of the insert 50 as described herein. The stacked suture pairs may substantially fill the suture passage 30. Even in the locked position, the stacked suture pairs may prevent the insert 50 from blocking the first and second openings of the suture passage 30 and/or from entering the suture passage 30 entirely. Each suture groove 72, 74 is at least two suture widths wide and at least one suture width deep.

Figures 29A, 29B, 29C, 29D:
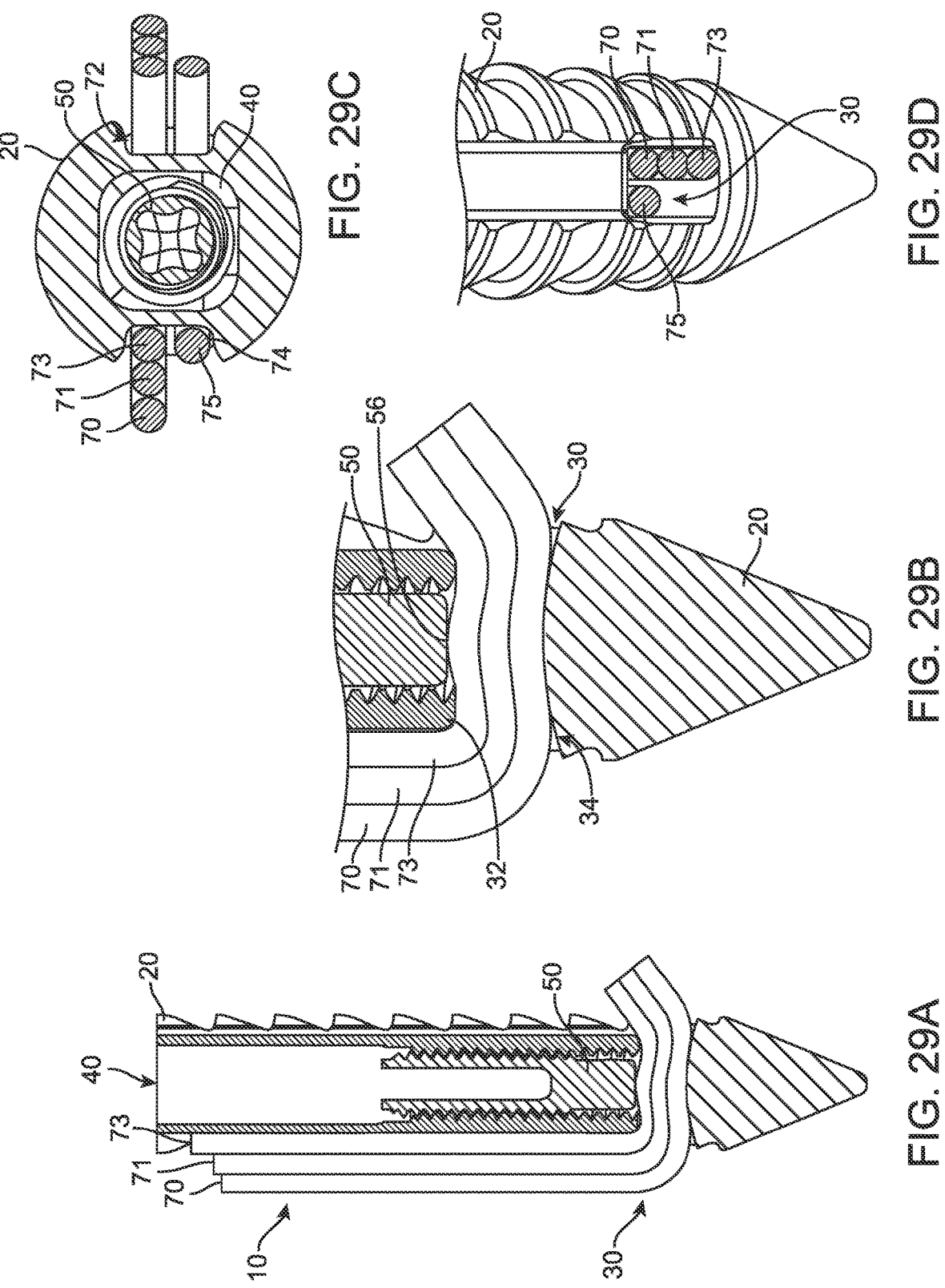
FIGS. 29A-29D show various views of four sutures locked within an anchor body, in accordance with some embodiments.

FIGS. 29A-29D show various views of four sutures 70, 71, 73, 75 locked within an anchor body 20. FIG. 29A shows a cross-sectional front view of the anchor body 20. FIG. 29B shows a cross-sectional front view of the suture passage 30. FIG. 29C shows a top view of the anchor body 20. FIG. 29D shows a perspective view of the suture passage 30. FIGS. 29A-29D are substantially similar to FIGS. 28A-28D except that the first suture 70, second suture 71, and third suture 73 are stacked together within the suture passage 30 while the fourth suture 75 is disposed next to the stack of sutures 70, 71, 73 within the suture passage 30.

FIG. 30 shows a cross-sectioned front view of another anchor system 100. FIG. 30 shows the insert 50 in a locked configuration. The insert 50 is disposed within a channel 40 extending along the longitudinal axis 16 of the anchor body 20 from a proximal opening 42 to a distal opening 44 in the proximal surface 32 of the suture passage 30. Longitudinal translation of the insert 50 within the channel 40 towards the distal surface 34 of the suture passage 30 from the unlocked configuration to the locked configuration compresses the suture 70 between the distal end 56 of the insert 50 and the distal surface 34 of the suture passage 30 in order to secure the suture 70 in the suture passage 30 as described herein. The distal surface 34 optionally comprises a pocket 39 which extends the channel 40 distally beyond the distal surface 34 of the suture passage 30. The pocket 39 provides a space into which the suture 70 can be wedged in order to lock the suture 70 therein. The edges of the distal surface 34 at the pocket 39 provide distinct points of force on the suture 70 to help secure it. The edges of the distal surface 34 at the pocket 39 may act as a first point of capture 79a and a second point of capture 79b. In some instances, it may be desirable to lock the suture 70 within a pocket 39 to prevent suture movement. In other instances, it may be less than desirable to stress the suture 70 at distinct points instead of spreading the force along a longer section of the suture 70. Such stress may damage the integrity of the suture 70 and/or wear down the suture faster than if a suture was secured using a suture anchor system that applied stress more evenly across the suture, such as other systems described herein. The choice of distal surface 34 configuration may depend on the surgical method, physiology, and/or surgeon preference.

Figures 31A, 31B, 31C:
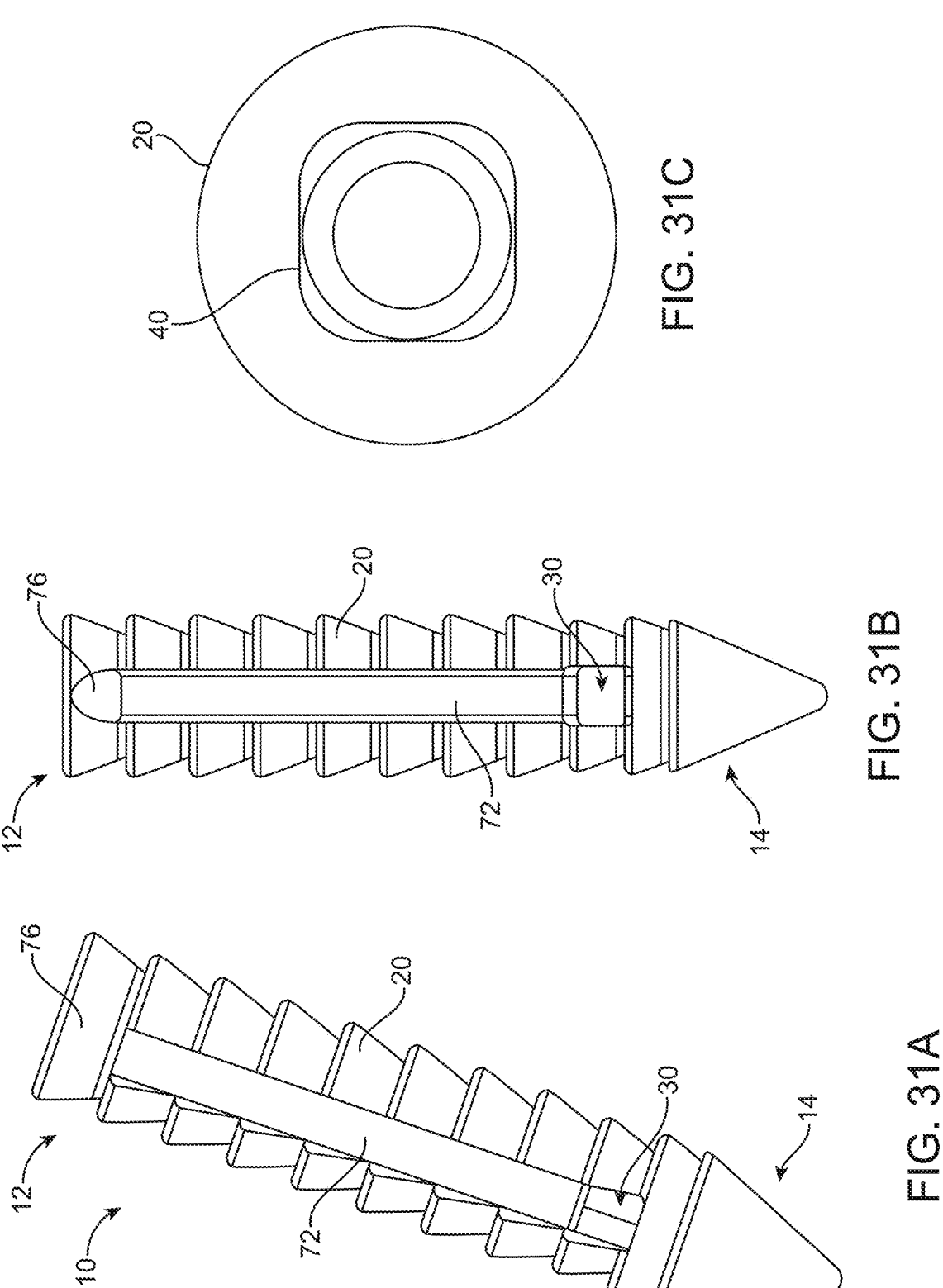
FIGS. 31A-31C show various views of an anchor body comprising suture grooves which taper at a proximal end of the anchor body, in accordance with embodiments.

FIGS. 31A-31C show various views of an anchor body 20 comprising modified suture grooves 72, 74 which terminate in a taper 76 at a proximal end 12 of the anchor body 20. FIG. 31A shows a perspective view, FIG. 31B shows a front view, and FIG. 31C shows a top view. The anchor 10 may be substantially similar to any of the anchors described herein except that one or both of the suture grooves 72, 74 terminate at distal end of a proximal taper 76 in the proximal end 12 of the anchor body 20. The proximal taper 76 extends proximally from suture grooves 72, 74 and reduces the depth of the suture grooves 72, 74 near the proximal end 12 of the anchor body 20 such that the suture grooves 72, 74 terminate at a point distal to the proximal end 12, before reaching the proximal end 12 of the anchor body 20. The portion of the proximal end 12 corresponding to the respective suture groove 72, 74 location tapers along proximal taper 76 from the suture grooves 72, 74 to the proximal surface of the anchor 10 such that the suture grooves 72, 74 are not visible at the proximal surface when looking at a top view of the anchor 10 as shown in FIG. 31C. In at least some instances, by not extending the suture grooves 72, 74 through the proximal end 12 of the anchor body 20, the proximal end 12 of the anchor body 20 will be more robust and stronger against suture forces than a proximal end 12 with grooves which extend through the proximal end 12 and can act as failure points (due to the reduced thickness and strength of materials thereat) when sufficient forces are applied thereto.

Figures 32A, 32B, 32C, 32D:
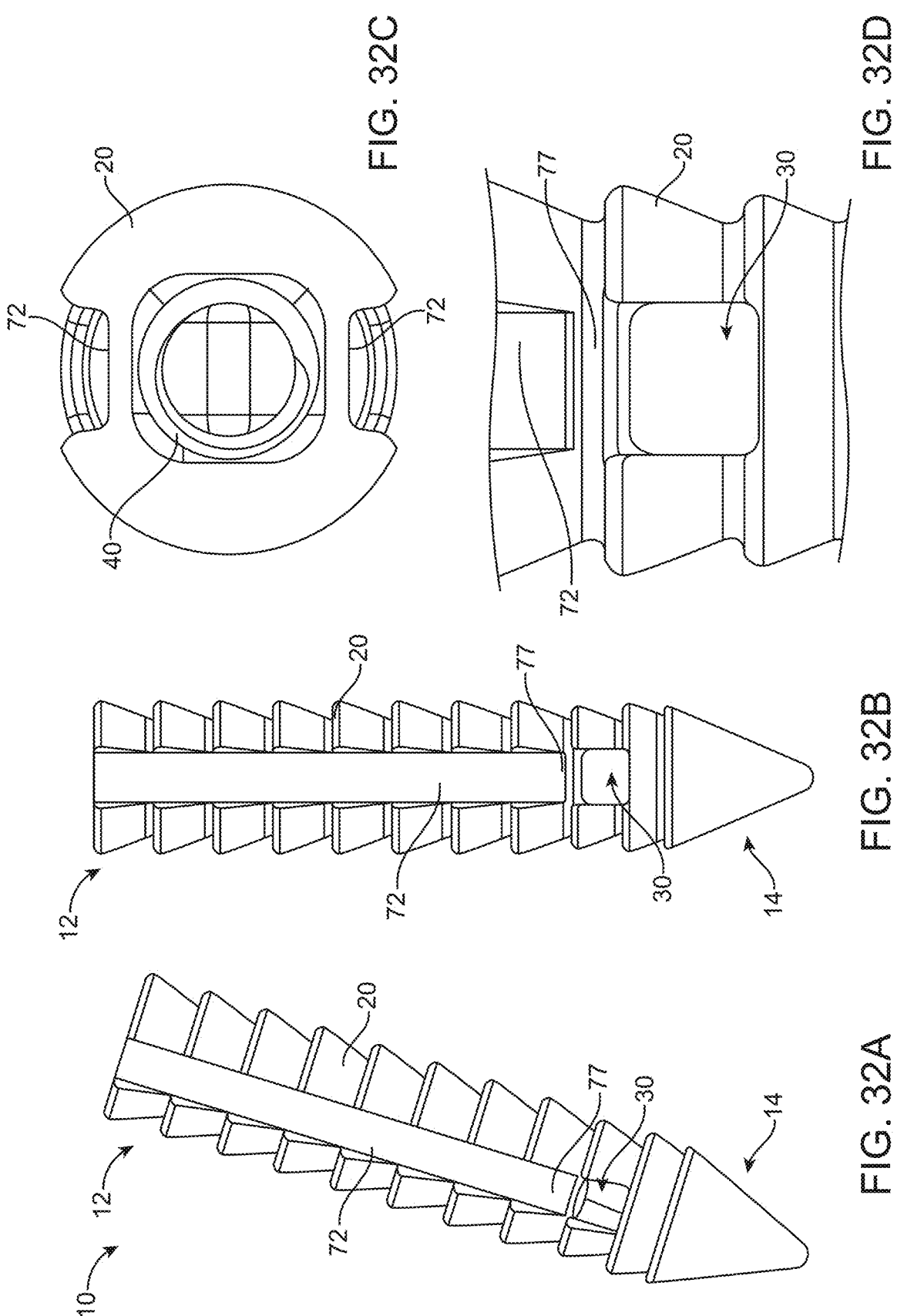
FIGS. 32A-32D show various views of an anchor body comprising suture grooves which taper adjacent a suture passage in the anchor body, in accordance with embodiments.

FIGS. 32A-32D show various views of an anchor body 20 comprising modified suture grooves 72, 74 which are proximally spaced from the suture passage 30 by an interruption 77 located therebetween. FIG. 32A shows a perspective view of the anchor body 20. FIG. 32B shows a front view of the anchor body 20. FIG. 32C shows a top view of the anchor body 20. FIG. 32D shows a front view of the suture passage 30. The anchor 10 may be substantially similar to any of the anchors described herein except that one or both of the suture grooves 72, 74 is intersected by or terminates at an interruption 77. The interruption 77 is configured to reduce the depth of the suture grooves 72, 74 at a predetermined location. The interruption 77 may be located anywhere along the length of the suture grooves 72, 74 as desired. For example, the interruption 77 may be a distal interruption which reduces the depth of the suture grooves 72, 74 just above the openings to the suture passage 30 such that the suture grooves 72, 74 terminate before reaching the suture passage 30. Stated another way, the suture grooves 72, 74 may be proximally spaced from the suture passage 30 via an interruption 77. In at least some instances, the interruption 77 adds thickness to the anchor body 20 in pre-determined strategic locations in order make the anchor body 20 more robust against off-axis insertion forces than a full groove 72, 74 with a minimum wall would be. For example, when an interruption 77 is placed distally (e.g., at or near the openings 36, 38) along each of the suture grooves 72, 74, the interruption(s) 77 may help prevent failure mode if accidentally hit off-axis when the suture passage 30 is just below the surface of the bone. It will be understood by one of ordinary skill in the art that the interruption(s) 77 can be located anywhere along the length of the anchor 10 where added wall thickness of the anchor body 20 may be beneficial. For example, locating the interruption 77 at the top of the openings 36, 38, away from the cortical bone layer, may be less impactful to suture movement.

Figures 33A, 33B, 33C:
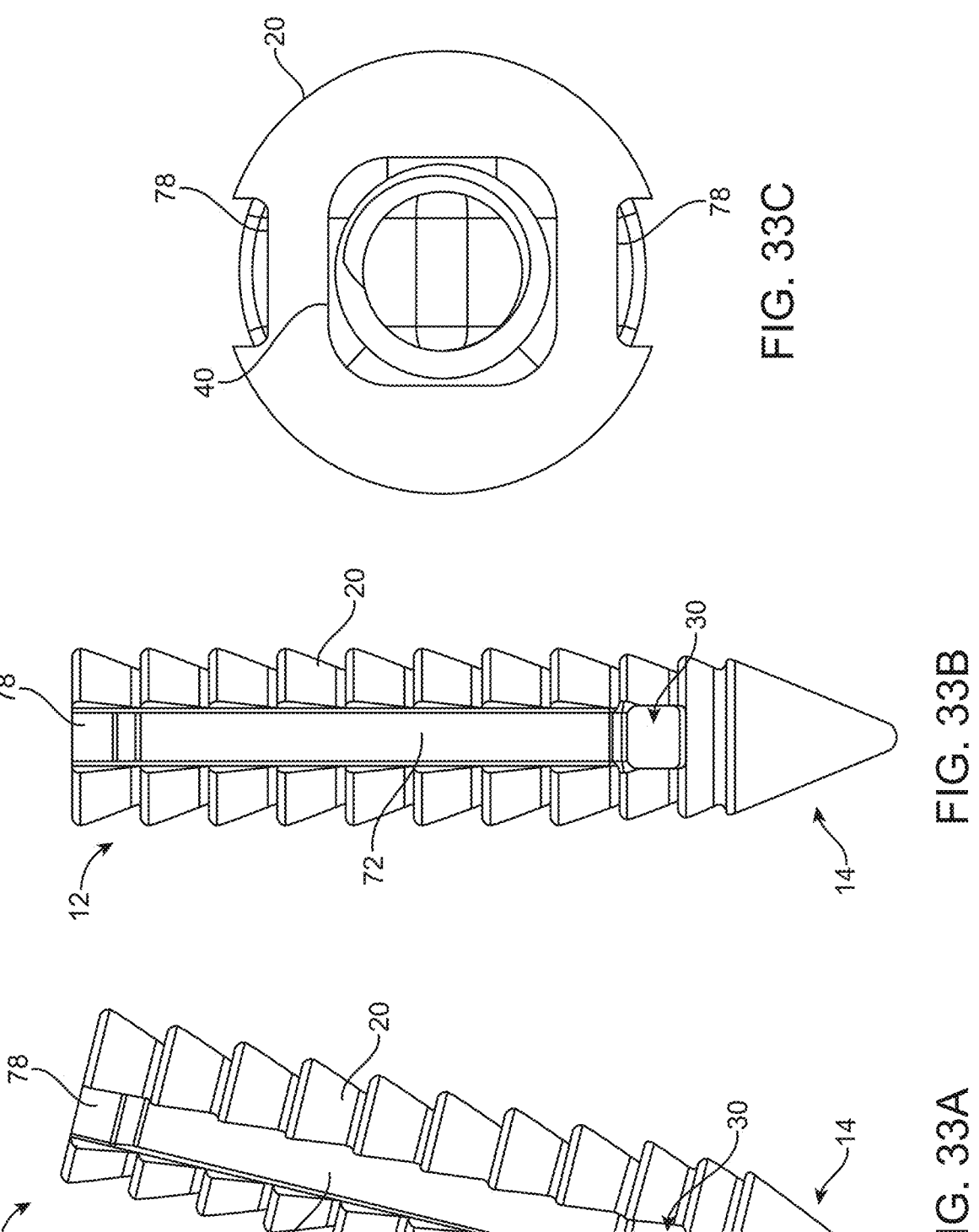
FIGS. 33A-33C show various views of an anchor body comprising suture grooves which reduce in depth at a proximal end of the anchor body, in accordance with embodiments.

FIGS. 33A-33C show various views of an anchor body 20 comprising modified suture grooves 72, 74 which reduce in depth 78 at a proximal end 12 of the anchor body 20. FIG. 33A shows a perspective view, FIG. 33B shows a front view, and FIG. 33C shows a top view. The anchor 10 may be substantially similar to any of the anchors described herein except that one or both of the suture grooves 72, 74 comprise a proximal step 78. The proximal step 78 reduces the depth of the grooves 72, 74 at the proximal end 12 of the anchor 10. For example, the proximal step 78 may reduce the depth of the grooves 72, 74 by about 50% at the proximal end 12 of the anchor 10 compared to the remainder of the grooves 72, 74 extending along the anchor body 20. In at least some instances, by decreasing the depth of the suture grooves 72, 74 at the proximal end 12 of the anchor body 20, the proximal end 12 of the anchor body 20 will be more robust and stronger against suture forces than a proximal end 12 with deeper grooves which extend through the proximal end 12 and can act as failure points (due to the reduced thickness and strength of materials thereat) when sufficient forces are applied thereto.

Figure 34:
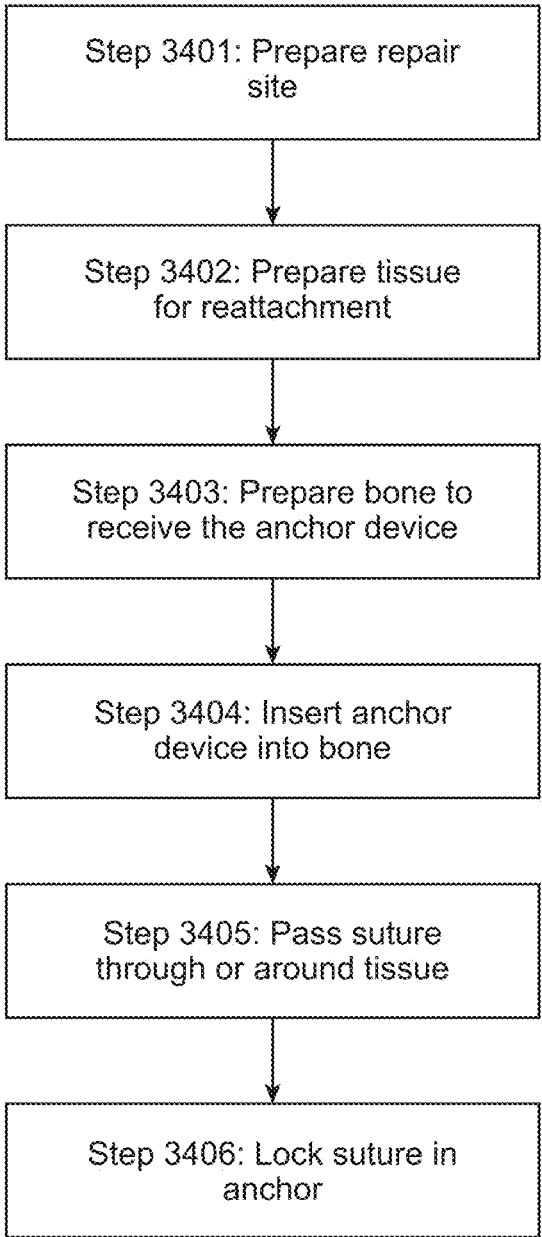
FIG. 34 shows an exemplary method of use for any of the anchor devices and systems described herein, in accordance with some embodiments.

FIG. 34 shows an exemplary method of use for any of the anchors 10 and systems 100 described herein.

At Step 3401, the repair site may be prepared. It will be understood by one of ordinary skill in the art that repair site may be prepared based on the anatomy, expertise of the surgeon, and/or preference of the surgeon. The anchor device 10 may, for example, accommodate an open, mini-open, and/or arthroscopic surgical approach as desired.

At Step 3402, the tissue for reattachment may be prepared according to a preferred surgical technique of the surgeon. In at least some instances, the anchor is pre-loaded with a suture. In other instances, the suture is not pre-loaded with a suture.

At Step 3403, the bone may be prepared to receive the anchor. For example, a pre-formed or pilot hole may be formed. In some embodiments, the pilot hole is formed using an anchor drill. In some embodiments, the pilot hole is formed using an awl. In some embodiments, a tip of an awl may be placed at a desired anchor site. The shaft may be aligned in line with the intended anchor axis orientation. A surgeon may then mallet the awl handle until a desired depth has been reached.

One or more guide tubes may be provided to accommodate varying anatomy and preferences. The guide tube(s) may be placed at a desired anchor site, the shaft of which may be aligned with the intended longitudinal axis of the anchor. A standard surgical power drill, or a specialized elongated anchor drill coupled to a surgical power drill, may be inserted into the guide tube handle until the drill is near the bone surface. One or more guide tubes may be provided on the guide shaft for visualization. The drill may be used to create a pilot hole. A collar on the drill may be configured to bottom out on the guide tube handle in order to ensure that the pilot hole does not exceed a pre-determined proper hole depth. The guide tube and/or drill may then be removed.

At Step 3404, the suture anchor may be inserted into the bone. For example, a delivery device as described herein may be positioned adjacent the bone (e.g., slid down a guide tube) with the distal end of the anchor body adjacent the bone. In some embodiments, the anchor is adjacent a pre-drilled hole in the bone. The delivery device may rotate, impact, or otherwise drive the anchor in to the bone. For example, the inner shaft and/or outer shaft and/or a separate mallet of delivery device may be used to drive the anchor device into the bone. The anchor body may be inserted until an optional circumferential laser mark on the delivery device, or other identifying mark or feature, is fully beneath the bone surface or otherwise desirably positioned relative to the bone.

In some embodiments, the bone may not require a pre-formed hole and the anchor may be self-punching (e.g., having a pointed tip). The anchor may be driven into the bone without pre-formation (e.g., drilling) of a hole.

At Step 3405, the suture 40 may be passed through or around the tissue intended to be secured to the bone as described herein. In some embodiments, Step 3405 occurs before Step 3404 such that the suture is passed through or around the tissue prior to the insertion of the anchor in the bone. In some embodiments, the suture is threaded through the anchor prior to Steps 3405 and 3404. In some embodiments, the suture is threaded through the anchor after Step 3405 but before Step 3404. In some embodiments, the suture is threaded through the anchor more than once, such as before and after Step 3405.

At Step 3406, the suture may be locked in the anchor. For example, a tail of the suture may be tensioned (e.g., pulled on) to a desired tension. In some embodiments, once the anchor is fully inserted, the suture tails may be pulled to the desired tension. Tails may be wrapped around the cleats on the inserter handle to maintain tension. Additionally, the knob may be rotated clockwise to drive the internal mechanism and secure the suture. The handle may be held steady during this process.

The delivery device may be configured to longitudinally translate an insert so as to engage a suture at the desired tension and may not be reversible (e.g., the anchor may comprise a one-way locking mechanism). In some embodiments, the anchor and/or insert may comprise an additional locking mechanism configured to lock the insert in the channel of the anchor after compressing the suture.

After locking the suture can be tied to another anchor and/or threaded through the suture passage as desired. Any extra length of suture exposed at the anchor interface may be cut and discarded.

Although the steps above show a method of repairing a tissue with an anchor device 10 in accordance with embodiments, a person of ordinary skill in the art will recognize many variations based on the teaching described herein. The steps may be completed in a different order. Steps may be added or deleted. Some of the steps may comprise sub-steps. Many of the steps may be repeated as often as necessary to repair a tissue.

As will be understood by one of ordinary skill in the art, any of the anchors, inserts, sutures, and delivery devices may be combined with one another or substituted for another and thus any number of combinations may be used. Additionally, various features of an anchor system have been described herein including anchor tip configurations, insert tip configurations, channel configurations, suture passage configurations, suture groove configurations, external retention features, suture types and numbers, delivery device configurations, driver tip configurations, and device coupler configurations. One of ordinary skill in the art will appreciate that these features may be combined with one another or substituted for another and thus any number of combinations may be used.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A suture anchor system for implantation in a subject, the system comprising:

an anchor comprising:

an anchor body having a proximal end, a distal end, a longitudinal axis, a first lateral side extending between the proximal end and the distal end, and a second lateral side extending between the proximal end and the distal end and opposite laterally of the first lateral side, a suture passage comprising a proximal surface and a distal surface and extending through the anchor body from a first opening in the first lateral side to a second opening in the second lateral side, wherein the distal surface comprises a first lateral plane extending from the first opening and a second lateral plane extending from the second opening, the first lateral plane and the second lateral plane coming together at a curved junction; and a channel extending along the longitudinal axis of the anchor body from a proximal opening in the proximal end of the anchor body to a distal opening in the proximal surface of the suture passage, wherein the channel does not extend past the distal surface of the suture passage; and an insert comprising an insert body having a proximal end and a distal end, wherein the insert is configured to translate longitudinally within the channel between the proximal end of the anchor body and the distal surface of the suture passage, wherein the anchor system has a locked configuration when the insert is translated distally such that the distal end of the insert compresses a suture extending through the suture passage against the distal surface of the suture passage whereby the suture cannot be adjusted relative to the suture passage, and the anchor system has an unlocked configuration when the insert is moved proximally from the locked configuration or is proximally positioned such that the suture can be adjusted relative to the suture passage.

2. The system of claim 1, wherein the distal end of the insert is shaped to correspond to the distal surface of the suture passage.

3. The system of claim 1, wherein the distal end of the insert is rounded.

4. The system of claim 1, wherein the distal end of the insert is v-shaped.

5. The system of claim 1, wherein at least a portion of an inner surface of the channel comprises threading and at least a portion of an outer surface of the insert body comprises correspondingly-shaped threading such that longitudinal translation of the insert occurs when the insert is rotated relative to the channel.

6. The system of claim 1, wherein the anchor or the insert further comprises a locking mechanism configured to lock the insert in the channel, wherein the locking mechanism comprises a ratchet, detent, or snap fit.

7. The system of claim 1, wherein the insert further comprises a device coupler configured to couple the insert to a delivery device, the delivery device comprising an inner shaft, wherein the device coupler comprises a cavity extending distally from the proximal end of the insert body, a proximal protrusion extending proximally from the proximal end of the insert body, and a driver configured to couple to the device coupler of the insert, and wherein the driver is translatably or rotationally disposed within the inner shaft of the delivery device.

8. The system of claim 1, wherein the first lateral side comprises a first suture groove extending parallel to the longitudinal axis of the anchor body from the first opening to the proximal end of the anchor body and wherein the second lateral side comprises a second suture groove extending parallel to the longitudinal axis of the anchor body from the second opening to the proximal end of the anchor body.

9. The system of claim 8, wherein the proximal end of the insert body comprises a proximal taper which terminates the first suture groove distal to the proximal end of the anchor body.

10. The system of claim 8, wherein the anchor body comprises an interruption which intersects or terminates the first suture groove proximal to the first opening.

11. The system of claim 8, wherein the first suture groove comprises a proximal step which reduces a depth of the first suture groove at the proximal end of the anchor body.

12. The system of claim 1, further comprising one or more external retention feature disposed on an outer surface of the anchor body.

13. The system of claim 12, wherein the one or more external retention feature comprises a bump, a ridge, a rib, a thread, a scale, an extension, a protrusion, or a projection.

14. The system of claim 12, wherein at least one of the one or more external retention feature is located distal of the first opening and the second opening.

15. The system of claim 1, wherein the distal end of the anchor body comprises a distal tip, wherein the distal tip is pointed, conical, tapered, or blunt.

16. The system of claim 1, wherein the anchor and the insert comprise polyetheretherketone (PEEK), polylactic acid (PLA), or polyglycolic acid (PGA).

17. The system of claim 1, further comprising at least two sutures disposed through the suture passage.

* * * * *